US012560161B2

(12) United States Patent
　　　Alexander et al.

(10) Patent No.:　US 12,560,161 B2
(45) Date of Patent:　　Feb. 24, 2026

(54) FLUID DELIVERY

(71) Applicant: KPR U.S., LLC, Mansfield, MA (US)

(72) Inventors: Samuel Alexander, Mansfield, MA (US); Georgia Burlingame, Mansfield, MA (US); Glenn Fournie, Mansfield, MA (US); Joseph Hudson, Mansfield, MA (US); Daniel Miller, Mansfield, MA (US); Tyler Palumbo, Mansfield, MA (US); Kevin Thomas, Mansfield, MA (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 19/072,093

(22) Filed: Mar. 6, 2025

(65) Prior Publication Data

US 2025/0283459 A1　　Sep. 11, 2025

Related U.S. Application Data

(60) Provisional application No. 63/562,445, filed on Mar. 7, 2024.

(51) Int. Cl.
　　　*F04B 49/10*　　　(2006.01)
　　　*A61M 5/142*　　　(2006.01)
　　　(Continued)

(52) U.S. Cl.
　　　CPC ....... *F04B 49/106* (2013.01); *A61M 5/14212* (2013.01); *A61M 5/14232* (2013.01);
　　　(Continued)

(58) Field of Classification Search
CPC .... A61M 5/14232; A61M 2005/14208; A61M 5/16886; A61M 2205/50; A61M 2205/3306; A61M 2005/1403; A61M 5/14212; A61M 5/14228; A61M 5/14526; A61M 5/16877; A61M 5/16809; F04B 43/12; F04B 49/106
See application file for complete search history.

(56) References Cited

U.S. PATENT DOCUMENTS 7,534,099 B2 *　5/2009　Knauper ............... A61M 5/172
　　　　　　　　　　　　　　　　　　　700/282
11,672,903 B2 *　6/2023　Biasi ................. A61M 5/14228
　　　　　　　　　　　　　　　　　　　417/279

(Continued)

*Primary Examiner* — Dominick L Plakkoottam
(74) *Attorney, Agent, or Firm* — ArentFox Schiff LLP

(57) ABSTRACT

Operating, based on an objective volume of a fluid aliquot to be delivered during a subinterval, a pump motor of a flow-control apparatus for a first motor duration at a beginning of the subinterval to deliver less than the objective volume. A change in position of a first component of the container relative to position of a second component of the container over the first motor duration is sensed. A volume of fluid delivered over the first motor duration based on the sensed change in position is estimated. A second motor duration, ending no later than the end of the subinterval, to deliver a remainder of the objective volume of the aliquot is determined based on a difference between the objective volume of the aliquot and the estimated volume of the aliquot. The pump motor is operated for the second motor duration targeting delivery of the remainder of the aliquot.

25 Claims, 12 Drawing Sheets

(51) Int. Cl.
   *A61M 5/145*        (2006.01)
   *A61M 5/168*        (2006.01)
   *F04B 43/12*        (2006.01)

(52) U.S. Cl.
   CPC .... *A61M 5/14526* (2013.01); *A61M 5/16877*
           (2013.01); *F04B 43/12* (2013.01); *A61M*
           *2005/14208* (2013.01); *A61M 5/14228*
           (2013.01); *A61M 2205/3334* (2013.01)

(56)               References Cited

U.S. PATENT DOCUMENTS

| | | | | |
|---|---|---|---|---|
| 2009/0318887 A1* | 12/2009 | Sacchetti | .............. | A61M 39/08 |
| | | | | 242/472.5 |
| 2010/0204645 A1* | 8/2010 | Dorsey | ............... | A61M 39/223 |
| | | | | 604/246 |
| 2014/0248159 A1* | 9/2014 | Marsh | ..................... | F04B 43/02 |
| | | | | 417/302 |
| 2015/0065988 A1* | 3/2015 | Holderle | ............... | A61M 5/172 |
| | | | | 604/67 |
| 2015/0174320 A1* | 6/2015 | Grant | ................ | A61M 5/14248 |
| | | | | 604/535 |
| 2016/0045399 A1* | 2/2016 | Wiesner | .............. | A61J 15/0088 |
| | | | | 604/73 |
| 2018/0236168 A1* | 8/2018 | Holderle | .......... | A61M 5/16886 |
| 2019/0154026 A1* | 5/2019 | Kamen | ................ | F04B 49/065 |
| 2020/0282135 A1* | 9/2020 | Breitweiser | ........... | A61M 5/008 |
| 2021/0393870 A1* | 12/2021 | Kessel | .............. | A61M 5/14244 |
| 2022/0379023 A1* | 12/2022 | Biermann | ......... | A61M 5/16886 |
| 2023/0147049 A1* | 5/2023 | Grant | ............... | A61M 5/14244 |
| | | | | 604/535 |

* cited by examiner

1200

1243

1246

1244

1245

1242

1264

1260

1266

1262

FLUID DELIVERY

CROSS REFERENCE TO RELATED APPLICATIONS

The present application claims the benefit of U.S. Pro. Pat. App. No. 63/562,445 filed Mar. 7, 2024, and entitled "FLUID DELIVERY," the disclosure of which is incorporated herein by reference in its entirety.

FIELD

Aspects of the disclosure generally relate to fluid delivery, and in some examples, to fluid delivery via a peristaltic pump to a patient from a syringe.

BACKGROUND

Administering medicine or nutrition to a patient who cannot intake the medicine or nutrition orally can be affected by utilizing peristaltic flow control systems. Typically, in such systems, fluid is delivered to the patient by a pump set including a flexible elastomeric tubing of a flow control apparatus, such as a peristaltic pump, which delivers fluid to the patient at a controlled rate of delivery. The peristaltic pump generally has a housing that includes a rotor operatively engaged to a motor through a gearbox. The rotor drives fluid through the flexible tubing of the pump set by the peristaltic action effected by reversible compression created by impingement, e.g., pinching, by one or more rollers on the rotor. Rotation of the rotor progressively compresses the elastomeric tubing that drives the fluid at a controlled rate. The pump set may have a valve mechanism for permitting or preventing fluid flow communication through the pump set. The flow control system may also have a controller that operatively regulates the one or more motors which effectively controls fluid flow.

Peristaltic pumps operate by delivering fluid in small charges interchangeably referred to herein as "aliquots." The rotor engages elastomeric tubing of the pump set, pinching off a portion of the elastomeric tubing and pushing fluid forward of the pinch point, e.g., closer to the patient than to the source of fluid toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally accurate and therefore especially useful in the administration of medication, therapeutic and nutritional fluids to the patient.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some aspects, the techniques described herein relate to a method of fluid delivery implemented in a flow control apparatus including tubing, a syringe of fluid in fluid communication with the tubing, and a pump motor operative to create a suction force on the fluid through the tubing to deliver a dose of the fluid from the syringe over a time interval, the dose including aliquots of the fluid deliverable over subintervals of the time interval, the method including: operating, based on an objective volume of an aliquot to be delivered during a subinterval, the pump motor for a first motor duration at a beginning of the subinterval to deliver less than the objective volume of the aliquot; sensing a change in a position of a plunger of the syringe over the first motor duration; estimating a volume of fluid delivered over the first motor duration based on the sensed change in position; determining a second motor duration to deliver a remainder of the objective volume of the aliquot, the second motor duration ending no later than the end of the subinterval and being determined based on the objective volume of the aliquot and the estimated volume of the aliquot; and operating the pump motor for the second motor duration targeting delivery of the remainder of the aliquot.

In some aspects, the techniques described herein relate to a flow control apparatus for fluid delivery including: a processor; memory in communication with the processor and storing instructions; tubing; a syringe in fluid communication with the tubing and adapted to store a fluid; and a pump motor operative, under control of the instructions executed by the processor, to create a suction force on a fluid in the syringe through the tubing to deliver a dose of the fluid from the syringe over a time interval, the dose including aliquots of the fluid deliverable over subintervals of the time interval, wherein the instructions, when executed by the processer are operative to cause the flow control apparatus to: operate, based on an objective volume of an aliquot to be delivered during a subinterval, the pump motor for a first motor duration at a beginning of the subinterval to deliver less than the objective volume of the aliquot; sense a change in a position of a plunger of the syringe over the first motor duration; estimate a volume of fluid delivered over the first motor duration based on the sensed change in position; determine a second motor duration to deliver a remainder of the objective volume of the aliquot, the second motor duration ending no later than the end of the subinterval and being determined based on a difference between the objective volume of the aliquot and the estimated volume of the aliquot; and operate the pump motor for the second motor duration targeting delivery of the remainder of the aliquot.

In some aspects, the techniques described herein relate to a computer program product for controlling fluid delivery in a flow control apparatus, the flow control apparatus including a processor; memory in communication with the processor and storing instructions; tubing; a syringe in fluid communication with the tubing and adapted to store a fluid; and a pump motor operative, under control of the instructions executed by the processor, to create a suction force on a fluid in the syringe through the tubing to deliver a dose of the fluid from the syringe over a time interval, the dose including aliquots of the fluid deliverable over subintervals of the time interval, the computer program product including instructions that when executed by the processer are operative to cause the flow control apparatus to: operate, based on an objective volume of an aliquot to be delivered during a subinterval, the pump motor for a first motor duration at a beginning of the subinterval to deliver less than the objective volume of the aliquot; sense a change in a position of a plunger of the syringe over the first motor duration; estimate a volume of fluid delivered over the first motor duration based on the sensed change in position; determine a second motor duration to deliver a remainder of the objective volume of the aliquot, the second motor duration ending no later than the end of the subinterval and being determined based on a difference between the objective volume of the aliquot and the estimated volume of the aliquot; and operate the pump motor for the second motor duration targeting delivery of the remainder of the aliquot.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which.

DETAILED DESCRIPTION

Figure 1:
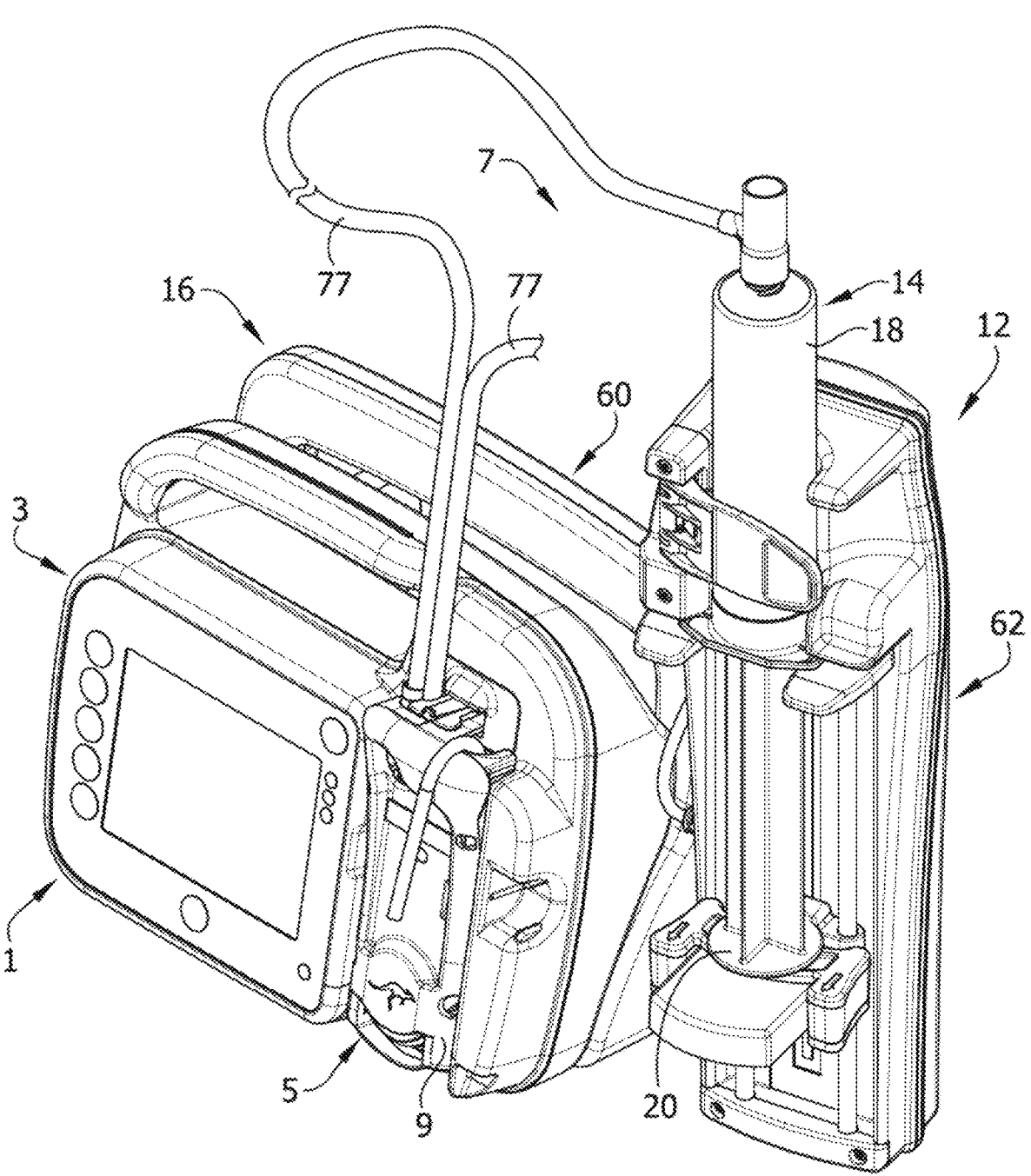
FIG. 1 is a perspective view of a feeding system including an enteral feeding pump, a pump support, a feeding set assembly and a syringe.
Figure 2:
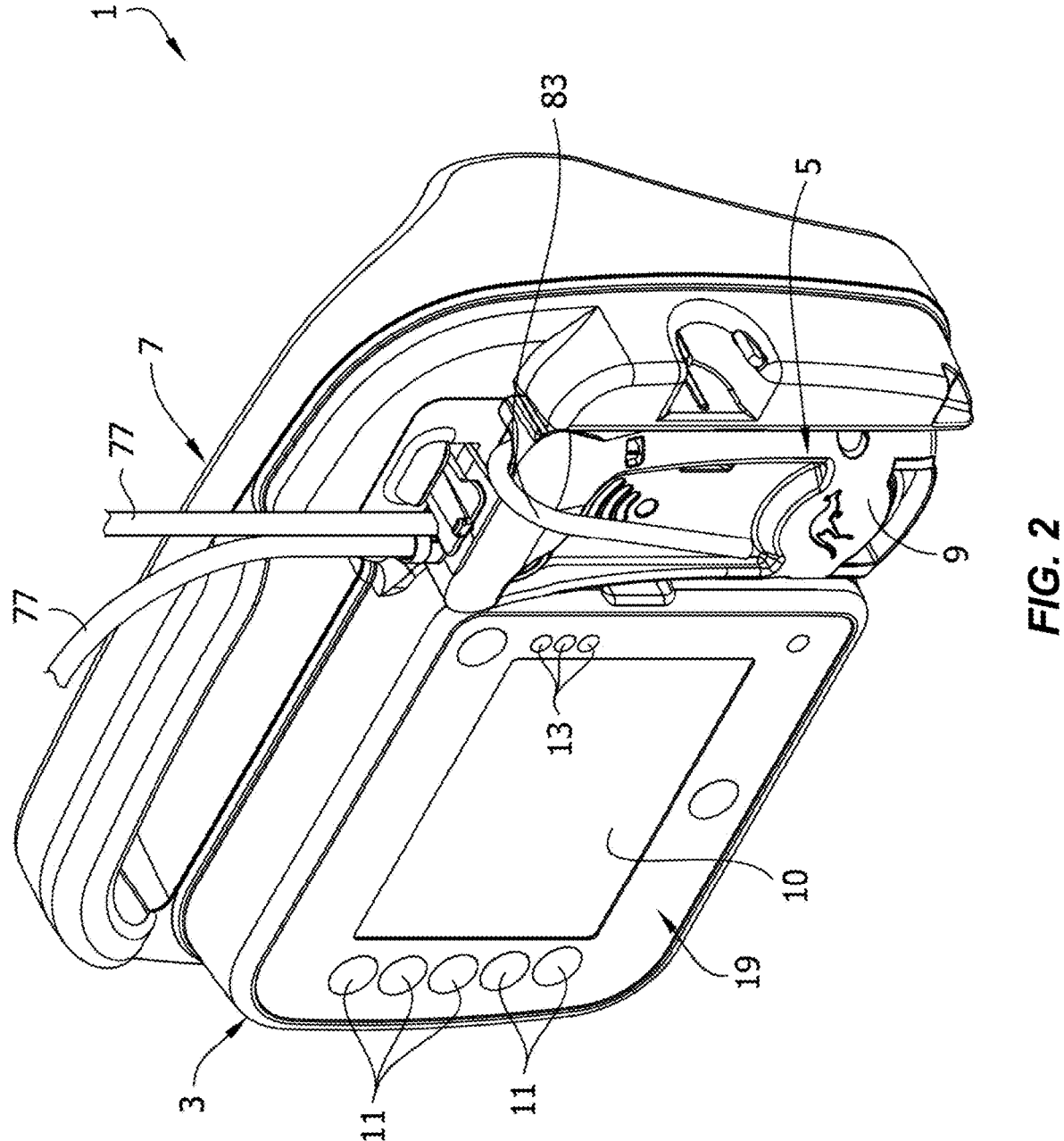
FIG. 2 is a fragmentary, perspective view of the feeding system including the enteral feeding pump, and part of the feeding set assembly.

In some existing flow control systems, the means for controlling the rate of delivery is to start and stop the motor of the pump, thereby controlling the number of aliquots, and not directly controlling the volume or rate of fluid delivered. In other existing flow control systems, the plunger of the syringe is driven directly. A need exists for alternate methods of controlling delivery of fluids to patients.

One or more aspects of the present disclosure pertain to fluid delivery via a peristaltic pump to a patient from a syringe. Any one or more advantageous features or structures that provide or facilitate any one or more of such features may be implemented in an enteral feeding pump employed in various commercial and industrial applications. Thus, although the detailed discussion is directed to an enteral feeding pump with a feeding set assembly including a cassette, any one or more features of the disclosure may be embodied or implemented in other pumps. For example, although the exemplarily discussed pump is a rotary peristaltic enteral feeding pump, the present disclosure has application to other types of peristaltic pumps (not shown), including medical infusion pumps. Additionally, one or more of the various features and aspects of the disclosure may be implemented in peristaltic pumps that use mechanisms other than rollers without departing from the scope of the present disclosure such as linear peristaltic pumps. Moreover, feeding set assemblies (not shown) that do not include cassettes may also be used within the scope of the present disclosure.

Referring now to the drawings, and in particular FIGS. 1-4, therein shown is one example enteral feeding pump 1 (interchangeably referred to herein as a "flow control apparatus"). The feeding pump 1 may comprise a housing 3 that is constructed so as to mount a cassette 5 of a feeding set assembly 7 (interchangeably referred to herein as a "pump set"). The feeding set assembly 7 may include a syringe assembly 12 connected to the cassette 5 via tubing 77. The cassette 5 of the feeding set assembly 7 is releasably attachable to the housing 3. In an illustrated aspect, a cassette shell 9 of the cassette is removably received in a cassette recess 6 (FIG. 4) in the housing 3. It will be appreciated that "housing" as used herein may include many forms of supporting structures (not shown), including without limitation multi-part structures and structures that do not enclose or house the working components of the pump 1. The pump 1 has a display screen 10 on the housing 3 capable of displaying information about the status and operation of the pump. Moreover, various aspects and features of the flow control apparatus can be implemented without the recess 6. One or more buttons 11 which can be proximate the display screen 10 can be provided for use in controlling and obtaining information from the pump 1, and one or more light emitting diodes 13 can provide status information for the pump.

The display screen 10 may be part of a front panel 19 of the housing 3 and may be removably attached to the housing. The enteral feeding pump further includes a pumping unit 23 (FIGS. 3 and 4) comprising a pump motor 27 (FIG. 8) connected to a rotor shaft (not shown). A battery (not shown) may be received in the housing 3 for powering the pump motor. A power source other than or in addition to the battery could be used to energize the pump including one or more prime motors which drive the pumping unit through the rotor shaft. The pumping unit 23 has a rotor 37, which can be coupled to the rotor shaft. The rotor 37 may include an inner disk 39, an outer disk 41, and rollers 43 mounted between the inner and outer disks for rotation relative to the disks about their longitudinal axes. The rollers 43 engage a tube 45 (FIG. 3) of the feeding set assembly 7 that forms part of the cassette 5 to deliver fluid through the feeding set assembly 7 to a subject when the cassette 5 is attached to the housing 3. For example, nutritional liquid (e.g., breast milk and/or fortifier) may be delivered to an infant using the pump 1, cassette 5, and feeding set assembly 7. Other fluids may also be delivered using the pump 1 without departing from the scope of the disclosure. In general, nutritional fluids, especially enteral nutrition for tube feeding, tend to be more viscous or thicker than most medicinal fluids due to the presence of macronutrients like proteins, carbohydrates, and fats. Medicinal fluids, on the other hand, are typically less viscous, as they are often diluted in solutions like saline or dextrose water.

In the illustrated aspects, the fluid in the syringe 14 is drawn from the syringe by a vacuum pressure applied by the pumping unit 23. In other words, the plunger is not used to drive delivery of fluid. However, aspects of the present disclosure may likewise be applicable if the fluid from the syringe 14 is delivered from the syringe in other ways, such as by driving the plunger into the barrel of the syringe.

Referring to FIGS. 1 and 5-7, therein shown is a pump support 16. The pump support 16 comprises a base 60 for supporting the pump support on a horizontal support surface such as a tabletop, and a syringe holder 62 attached to the base for securing the syringe 14 to the base. It will be understood that the base could also be configured to support the pump on other surfaces or structure, including without limitation, non-horizontal surfaces. As will be explained in greater detail below, the holder 62 may be configured to detect the presence and/or size of the syringe 14 mounted to the holder. In one aspect, the syringe 14 and syringe holder 62 may comprise the syringe assembly 12. However, the syringe 14 alone or the syringe and tubing connected to the syringe may comprise the syringe assembly. The pump support 16 may support the syringe 14 relative to the pump 1 when the pump is mounted on the pump support. Alternatively, the pump support 16 may be configured as a syringe stand such that the holder receives and supports the syringe 14 but does not also mount and/or support the pump 1. The syringe 14 may be a conventional syringe including a barrel 18, which may be graduated, and a plunger 20 slidably received in the barrel. The syringe 14 may also be of other configurations without departing from the scope of aspects of the present disclosure.

The base 60 may have a flat bottom surface 64 for resting the base on a horizontal support surface. A back wall 66 may extend upward from the bottom surface 64 and mounts the pump 1 to the base 60. A pair of side walls 68 may extend laterally from the back wall 66 opposing opposite sides of the pump 1 when the pump is mounted to the base 60. The back wall 66 and side walls 68 together may define a receiving space for the pump 1. The back wall 66 may attach to the holder 62 to locate the holder relative to the base 60.

Figure 5:
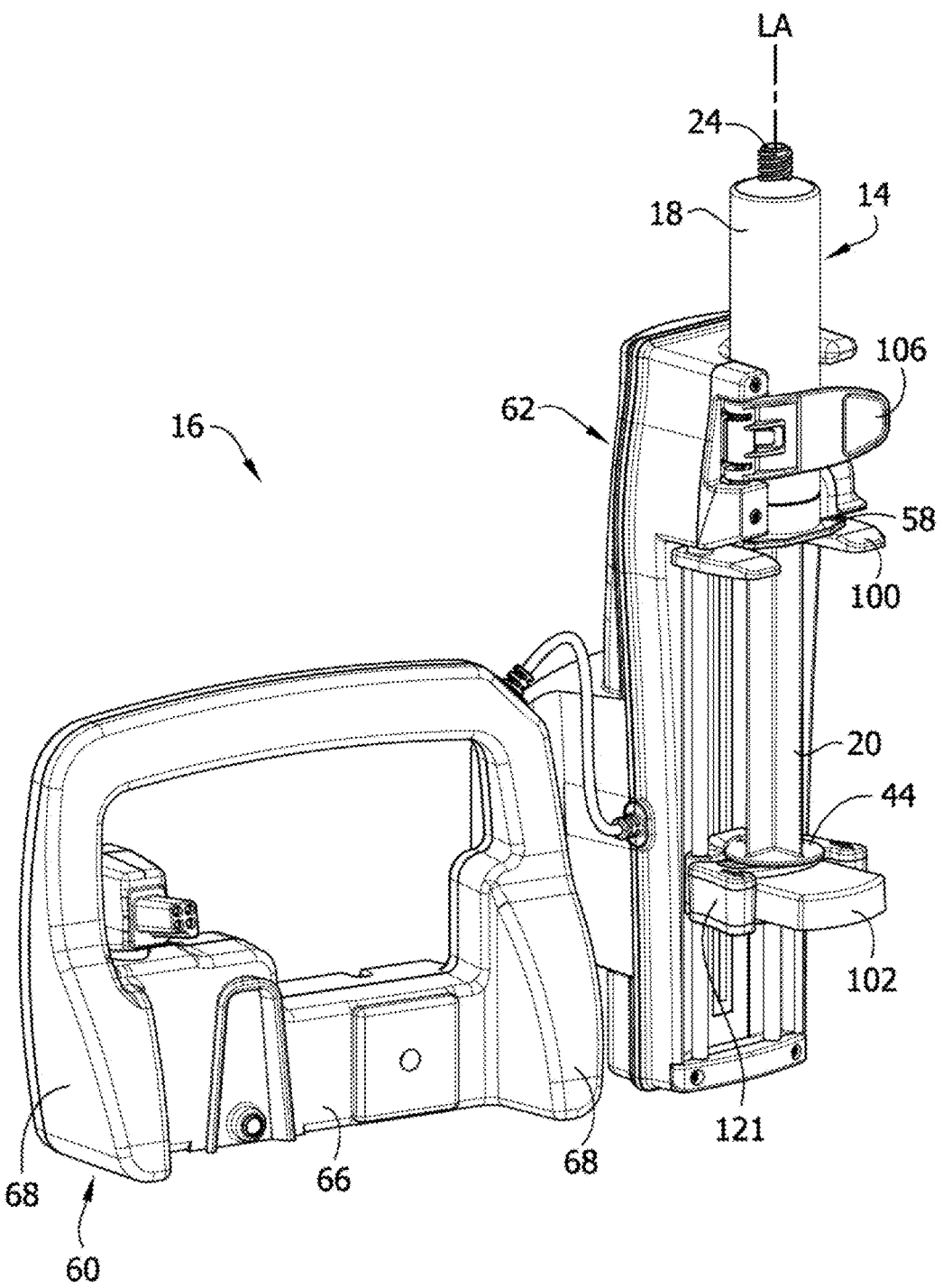
FIG. 5 is a front perspective view of a pump support and syringe of the feeding set assembly.
Figure 6:
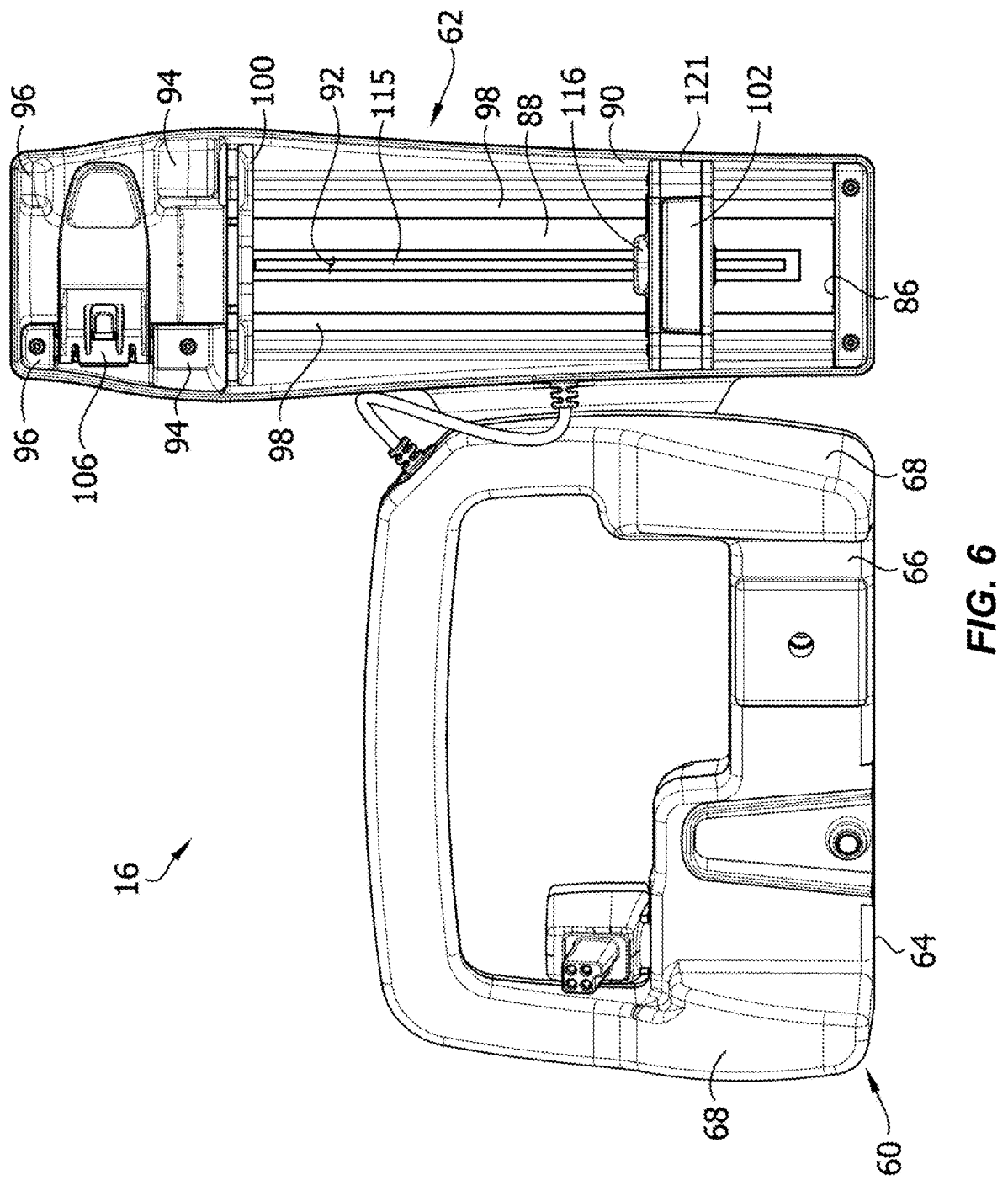
FIG. 6 is a front perspective view of the pump support.
Figure 7:
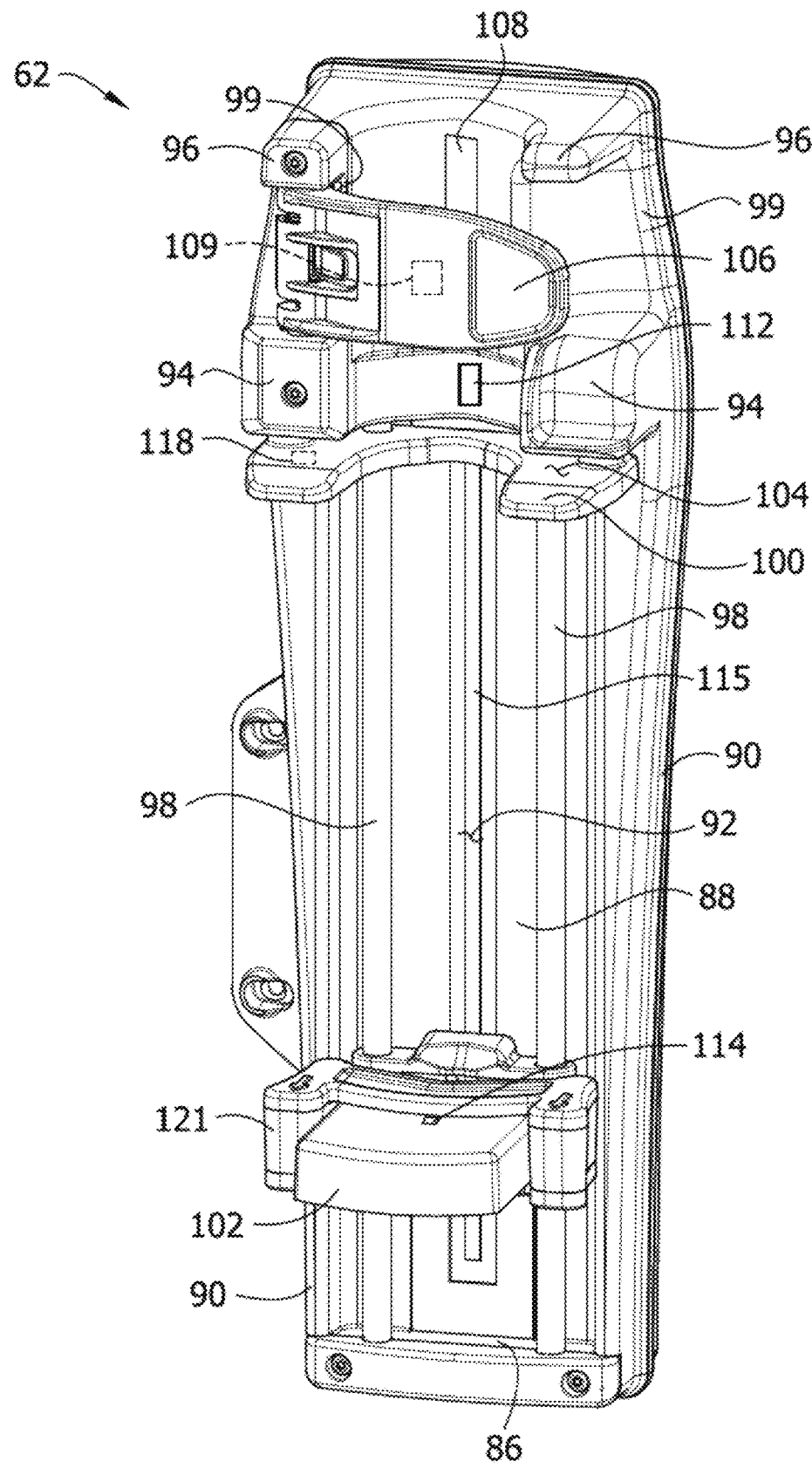
FIG. 7 is a front perspective view of a syringe holder of the pump support.

Referring to FIG. 6 and FIG. 7, the syringe holder 62 may include a floor 86, a rear wall 88 extending from the floor, and opposing side walls 90 extending laterally from the rear wall and away from the floor. The floor 86, rear wall 88, and side walls 90 together may define a receiving space 92 for at least a portion of the syringe 14. A first pair of flanges 94 may extend from respective side walls 90 of the holder 62 near a top of the holder. Each side wall 90 may have a recessed portion 99 above the flange 94 forming a second pair of flanges 96 longitudinally spaced upward from the first pair of flanges 94. A portion of the barrel 18 of the syringe 14 may be received between the first pair of flanges 94 and between the second pair of flanges 96. The flanges 94, 96 may prevent movement of the barrel 18 in the holder 62 along an axis parallel to the rear wall 88. A pair of rails or guides 98 may extend between the floor 86 and the first pair of flanges 94. A U-shaped plate 100 (broadly, a flange plate) may be fixedly disposed at a top end of the rails 98, and a slide plate 102 (broadly, a plunger follower) may be disposed around a bottom end of the rails and configured to move or slide along the rails in response to movement of the syringe plunger 20. A gap 104 may be formed between the first pairs of flanges 94 and the flange plate 100. The gap 104 may be configured to receive a flange 58 of the barrel 18 of the syringe 14 (FIG. 5). The length of the gap 104 may be slightly smaller than a thickness of the flange 58. Thus, the flange 58 may be held in a fixed position between the flanges 94 and the plate 100, thereby fixing the barrel 18 against longitudinal movement within the holder 62. Further, when the syringe 14 is received in the holder 62, a flange 44 of the plunger 20 may be held between a slide 121 (broadly, a catch) and the slide plate 102. For example, the slide 121 may be actuatable to away from the rear wall 88 to provide clearance for the plunger flange 44. The slide 121 can then be moved back toward the rear wall 88 to secure the plunger flange 44 to the slide plate 102. As will be explained in greater detail below, fluid being drawn from the barrel 18 of the syringe 14 may cause the plunger 20 to move away from the floor 86. Because the flange 44 of the plunger 20 may be captured between the slide 121 and slide plate 102, the movement of the plunger may be followed by the slide plate 102 which may move along the rails 98 in response to movement of the plunger. A connection arm 110 may extend from one of the side walls 90 and may be configured to attach the holder 62 to the base 60.

Referring to FIGS. 1 and 7, a sensor 115 may be attached to the rear wall 88 of the holder 62 to detect placement of the syringe 14 in the holder and/or the movement of the plunger 20 of the syringe relative to the holder. In the illustrated aspect, the sensor 115 may comprise a linear potentiometer or may comprise a linear resistive potentiometer. However, other sensor types may be used without departing from the scope of aspects of the disclosure. For example, the sensor 115 may be a hall effect sensor, multiple hall effect sensors or an array thereof, and/or an array of hall effects devices. When the syringe 14 is properly loaded on the holder 62, a ball detent 116 on the holder (e.g., slide plate 102) may engage (i.e., come into direct contact with) the sensor 115. For example, the plunger 20 may cause the ball detent 116 to come into contact with the sensor 115. In one aspect, the circuit of the senor 115 may be normally closed. However, the pressure from the ball detent 116 may divide the voltage causing the analog signal to change indicating that the syringe 14 has been properly loaded onto the holder 62. If the change in the analog to digital converter (ADC) value is not detected upon loading the syringe 14 onto the holder 62, the pump 1 may continue to prompt the user to load the syringe on the holder. Generally, the sensor 115 and ball detent 116 may comprise a first syringe presence detection assembly, and a process of detecting the presence of the syringe 14 using the sensor and ball detent may comprise a first syringe presence detection routine that is operable by a controller 72 of the pump 1 operatively connected to the sensor.

Additionally, a flange sensor 112 may be associated with (e.g., disposed in or attached to) the holder 62, and a magnet 118 may be associated with (e.g., disposed in or attached to) plate 100. In one aspect, the magnet 118, may for example comprise one or more permanent magnets. A permanent magnet may, for example, comprise a magnetized ferromagnetic material or a material containing magnetized material(s) and/or particles. Because the plate 100 may be cantilevered off of the rear wall 88, and the gap 104 may be slightly smaller than a thickness of the barrel flange 58, a free end of the plate may be deflectable (i.e., movable downward) upon receiving the barrel flange in the gap. The downward deflection of the plate 100 causes movement of the magnet 118, which can be sensed by the flange sensor 112. For example, the flange sensor 112 may be a hall effect sensor detecting a change in the magnetic field strength caused by the movement of the magnet 118. This change in magnetic field strength may provide a secondary indication of the presence of the syringe 14 in the holder 62. The flange sensor 112 and magnet 118 may comprise a second syringe presence detection assembly, and a process of detecting the presence of the syringe 14 using the sensor and magnet may comprise a second syringe presence detection routine that is operable by the controller 72 of the pump 1 operatively connected to the sensor.

A door or gate 106 (interchangeably referred to herein as a syringe clip) may be pivotally attached between one of the first pair of flanges 94 and one of the second pair of flanges 96 and moveable between an open position to allow the syringe 14 to be received in the receiving space 92, and a closed position for retaining the syringe (i.e., barrel 18) in the receiving space. A sensor 108 (FIG. 7) may be provided on the holder 62 to detect the position of the gate 106 as it may be moved between the open and closed positions. For example, a magnet 109 may be located in the gate 106 such that a change in magnetic field is detected based on the angular position of the magnet relative to the sensor 108. Thus, the angular position of the gate 106 may be detected as the gate may be opened to provide a passage for the syringe barrel 18 to be received in the holder 62, and then may be closed around the barrel to secure the syringe to the holder. As will be explained in greater detail below, a determination of the size of the syringe 14 can be made using the angular position of the gate 106 when the barrel 18 is secured in the holder by the gate. In one aspect, the sensor 108 may comprise an angular sensor. In some aspects, the angular sensor may be embedded within or otherwise located at the surface of or approximately at the surface of the rear wall 88 or a body of the holder 62. In some aspects, the angular sensor may be on and/or within a flexible circuit board or flexible printed circuit board. In some aspects, the flexible printed circuit board and/or the location of the angular sensor may allow the surfaces of the body of the holder to be easily cleaned and/or disinfected. The sensor 108 and magnet 109 may comprise a syringe size detection assembly.

Figure 8:
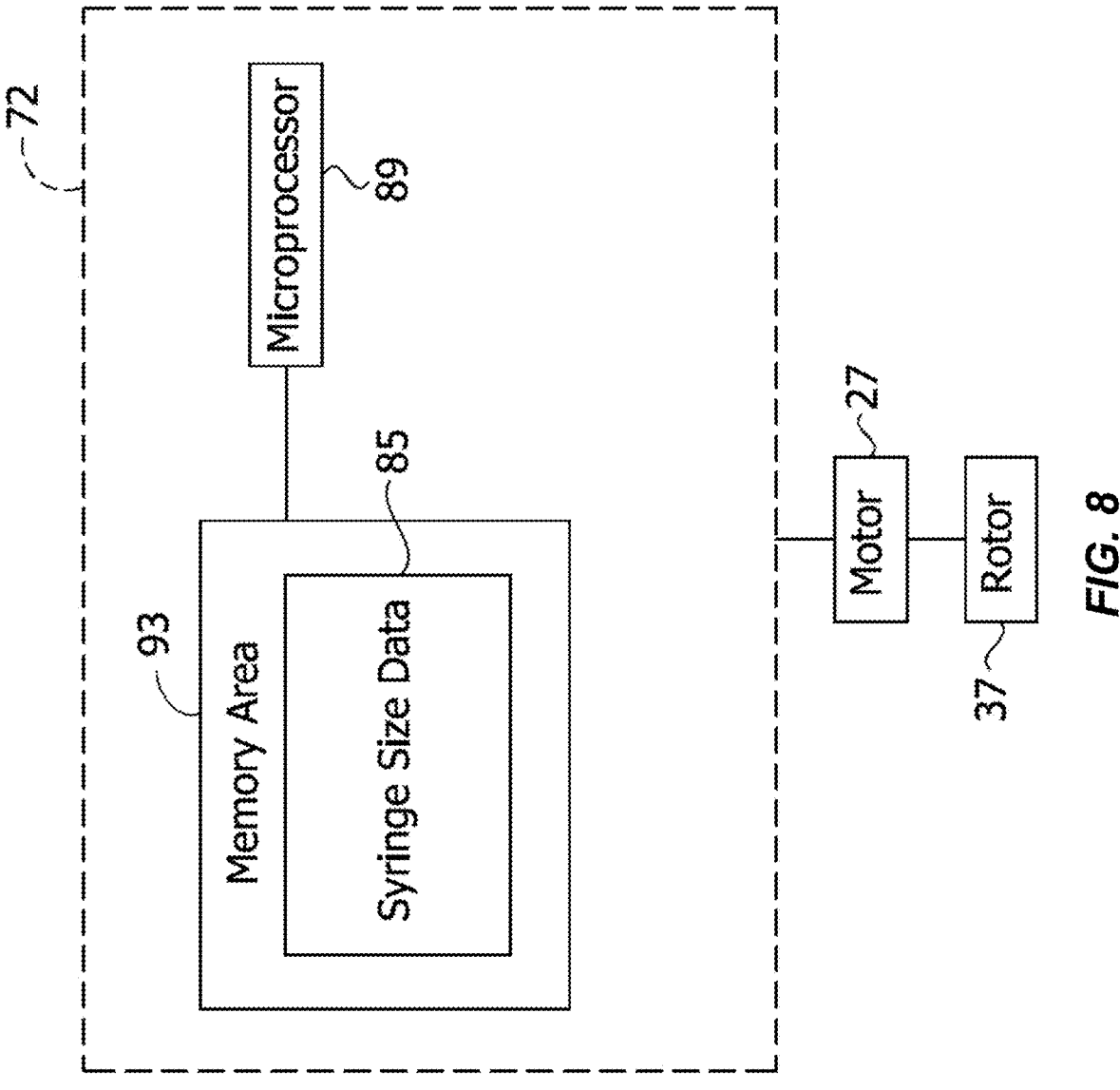
FIG. 8 is a block diagram showing components of the enteral feeding pump that may be utilized to implement one or more aspects disclosed herein.
Figure 9:
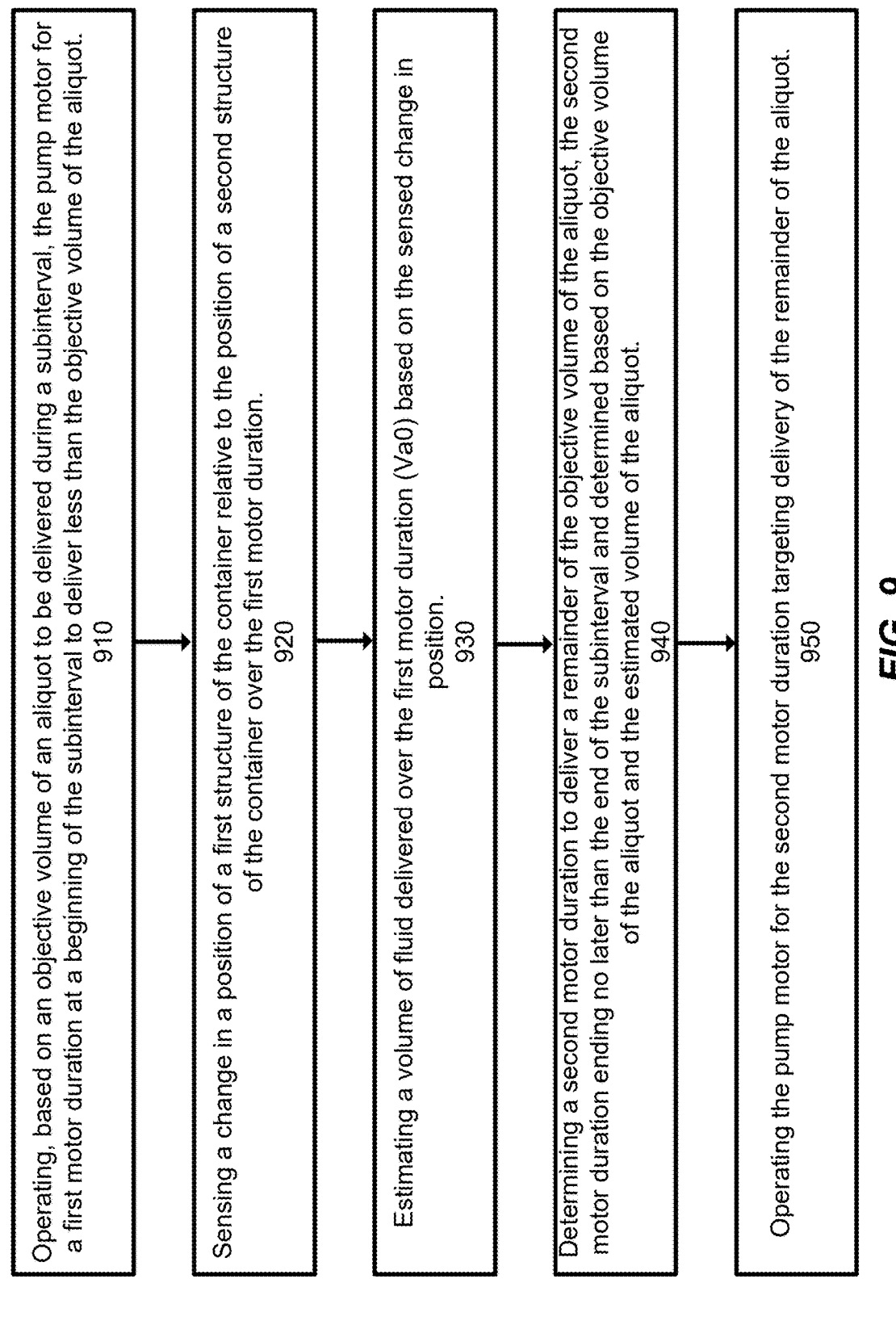
FIG. 9 is a flow chart of a method, according to examples of aspects disclosed herein.

Referring to FIGS. 7-9, a controller 72 in the pump 1 may initiate a syringe size detection routine to determine the size of the syringe received in the holder 62. Once the gate 106 has fully secured the barrel 18 of the syringe 14 to the holder 62, a position of a line of demarcation between the north and south pole on the magnet 109 may be detected by the sensor 108 at 200. An angle of the magnet 109 may then be determined by the sensor 108 using integrated hall devices at 202. A proportional digital value of the magnetic field may then be communicated to the controller 72 at 204. The magnetic field signal may be compared to statistically generated corresponding digital size range data 85 previously programmed and saved in a memory 93 of the controller 72 at 206. If the magnetic field angle falls within one of the programmed size ranges and the presence of the syringe 14 was previously detected and confirmed by the two syringe presence detection routines, then the size of the syringe may be indicated by the pump 1 at 208. For example, the display screen 10 of the pump 1 may show the size syringe that has been detected (e.g., 60 mL syringe). The pump 1 may then prompt the user to confirm that the detected syringe size is correct at 210. For instance, the pump 1 may display a question on the display screen 10 with the option to select "Yes" or "No" to confirm that the detect syringe size is correct. If, however, the magnetic field angle falls outside of the programmed size ranges, the pump 1 may display a prompt on the display screen 10 for the user to select the syringe size from a list of options or manually input the syringe size at 212. For example, the display screen 10 may show four syringe sizes and an "other" option for the user to select from. Once the syringe size has been detected or selected by the user, the pump 1 may be operated to pump fluid from the syringe assembly. In one aspect, operation of the pump 1 to deliver fluid from the syringe 14 may be prevented unless both the first and second syringe presence detection routines indicate that the syringe is present, the syringe size detection routine determines the size of the syringe, and the syringe size has been confirmed or identified.

The holder 62 may also be configured to detect movement/change of position of the plunger 20 during pumping of the fluid from the syringe 14. A contact 114 of the potentiometer 115 may be disposed on a movable portion of the holder 62, such as the slide plate 102, so that movement of the slide plate causes the contact to move along the potentiometer 115. Because the barrel 18 may be held in a fixed position in the holder 62, as fluid is withdrawn from the barrel, the plunger 20 may move into the barrel. The flange 44 of the plunger 20 may be fixed to the slide plate 102 as the plunger moves into the barrel 18 causing the slide plate to move along the rails 98. Therefore, in some aspects, movement of the contact 114 may represent the movement of the plunger 20 relative to the barrel 18 and holder 62 caused by the feeding fluid being drawn out of the syringe 14. Stated another way, the movement of the contact 114 may correspond to the distance of advancement of the plunger 20 into the barrel 18. Further, an outer diameter of the barrel 18 can be extrapolated from the angular position that the gate 106 to identify the appropriate calibration constant to use which relates change in plunger 20 position to a change in fluid volume delivered. Alternatively, as the cross-sectional area of the internal cavity of the barrel 18 may be known from the detection of the syringe size, the potentiometer 115 can be calibrated so that the movement of the contact 114 indicates the volume of fluid expelled from the syringe 14. In particular, by knowing the inner diameter of the barrel 18 of the syringe 14, in combination with the distance the slide plate 102/plunger 20 has moved, the volume of fluid delivered from the syringe 14 can be determined. The potentiometer 115 may be electrically connected to the controller 72 for receiving position signals from the potentiometer 115 indicating the movement of the slide plate 102. The controller 72 may be located in the pump 1 or may be located remote from the pump 1 and in communication with the pump 1. For example, the controller 72 may be located in the pump support 16. In an aspect where the plunger 20 may be held in a fixed position and the barrel 18 may move relative to the plunger, the movement of the contact may represent the movement of the barrel 18.

One example feeding set assembly 7 may be used for enteral feeding of neonates to achieve metered fluid delivery using the enteral feeding pump 1. In such a method, the enteral liquid is drawn into the syringe 14 by pulling back on the plunger 20. The amount of enteral liquid may be measured using graduation markings on the barrel 18 of the syringe 14. With the syringe 14 loaded in the holder 62 of the pump support 16 and attached to the tubing 77, the pump 1 may be configured for delivering the feeding solution in the syringe to a subject. Operation of the pump 1 may cause the rollers 43 to engage the tube 45 in the cassette shell 9 to pump the feeding solution from the syringe 14 to the subject. Engagement of the tube 45 by a roller 43 may cause the rollers 43 to occlude the tube 45. If the pump support 16 is configured such that the syringe is oriented in a vertical orientation with the tip 24 facing upward, gravity may not assist in drawing feeding fluid out of the syringe. Additionally, there may be no direct actuation of the plunger 20 that forces fluid upward out of the barrel 18. Thus, as the rotor 37 rotates to occlude the tube 45 with the rollers 34, air, not liquid, may be first drawn out of the inlet tubing 77 and barrel 18 of the syringe 14 which increases the vacuum pressure within the syringe. After a sufficient number of rotor rotations, vacuum pressure may be created in the inlet tubing 77 and syringe 14. Continued rotation of the rotor 37 may draw feeding fluid from the barrel 18 into the inlet tubing 77 through the inlet port 69 and tubing 45 of the cassette shell 9 to be pumped by the pump 1 into the outlet tubing 83 to the subject.

The pump 1 can be programmed or otherwise controlled for operation in a desired manner. For instance, the pump 1 can begin operation to provide feeding fluid from the syringe 14 to the subject. A user, such as a caregiver, may select (for example) the amount of fluid to be delivered, the flow rate of the fluid, and the frequency of fluid delivery. The pump 1 may have controller 72 (FIG. 8) including a processor such as a microprocessor 89 that allows it to accept programming and/or to include pre-programmed operational routines, e.g., algorithms, which can be initiated by the user. The controller 72 may also be connected to the pump motor 27 for controlling its operation to actuate the rotor 37.

Figure 3:
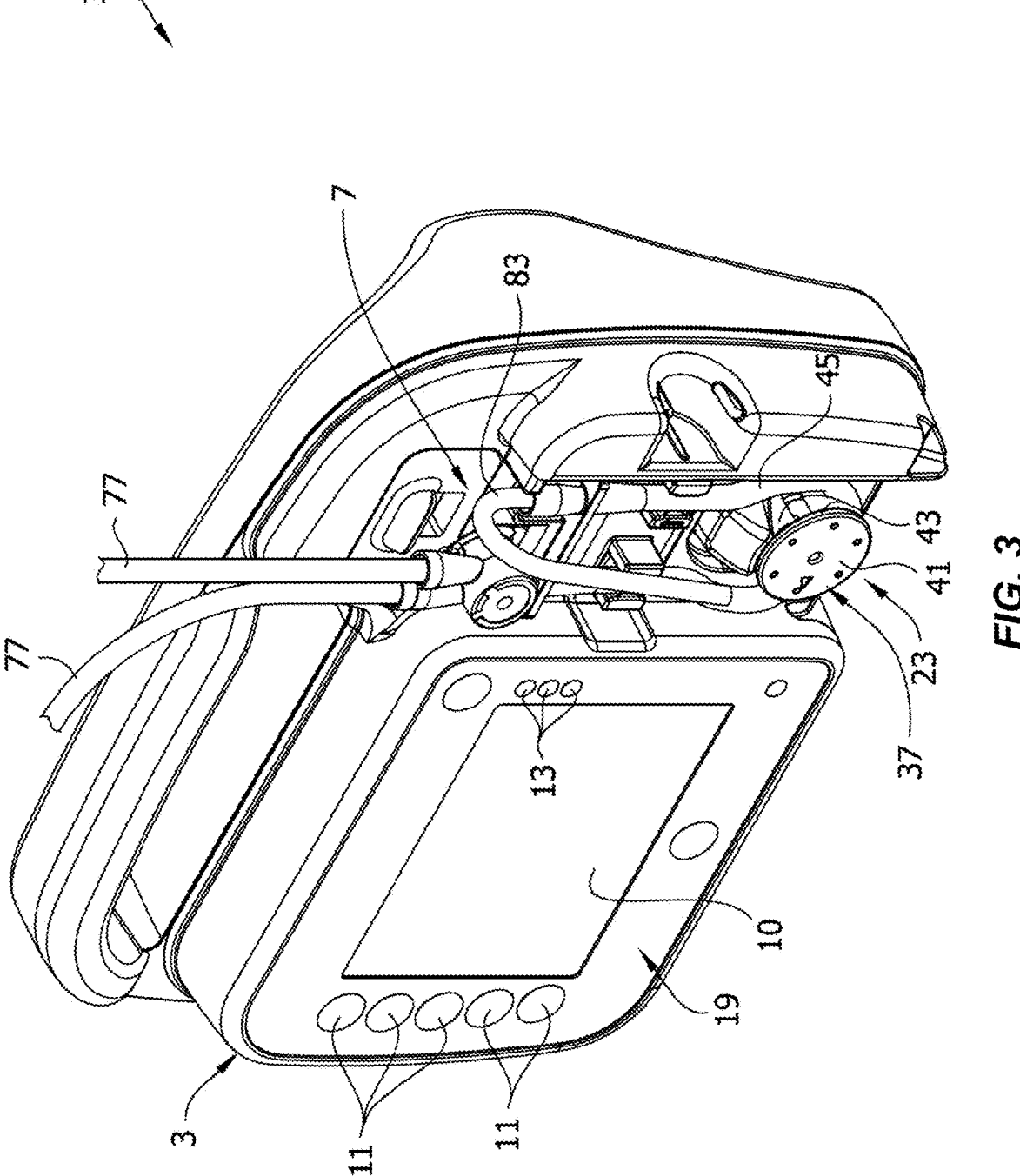
FIG. 3 is the perspective view of FIG. 2, but with portions of a cassette of the feeding set assembly removed.
Figure 4:
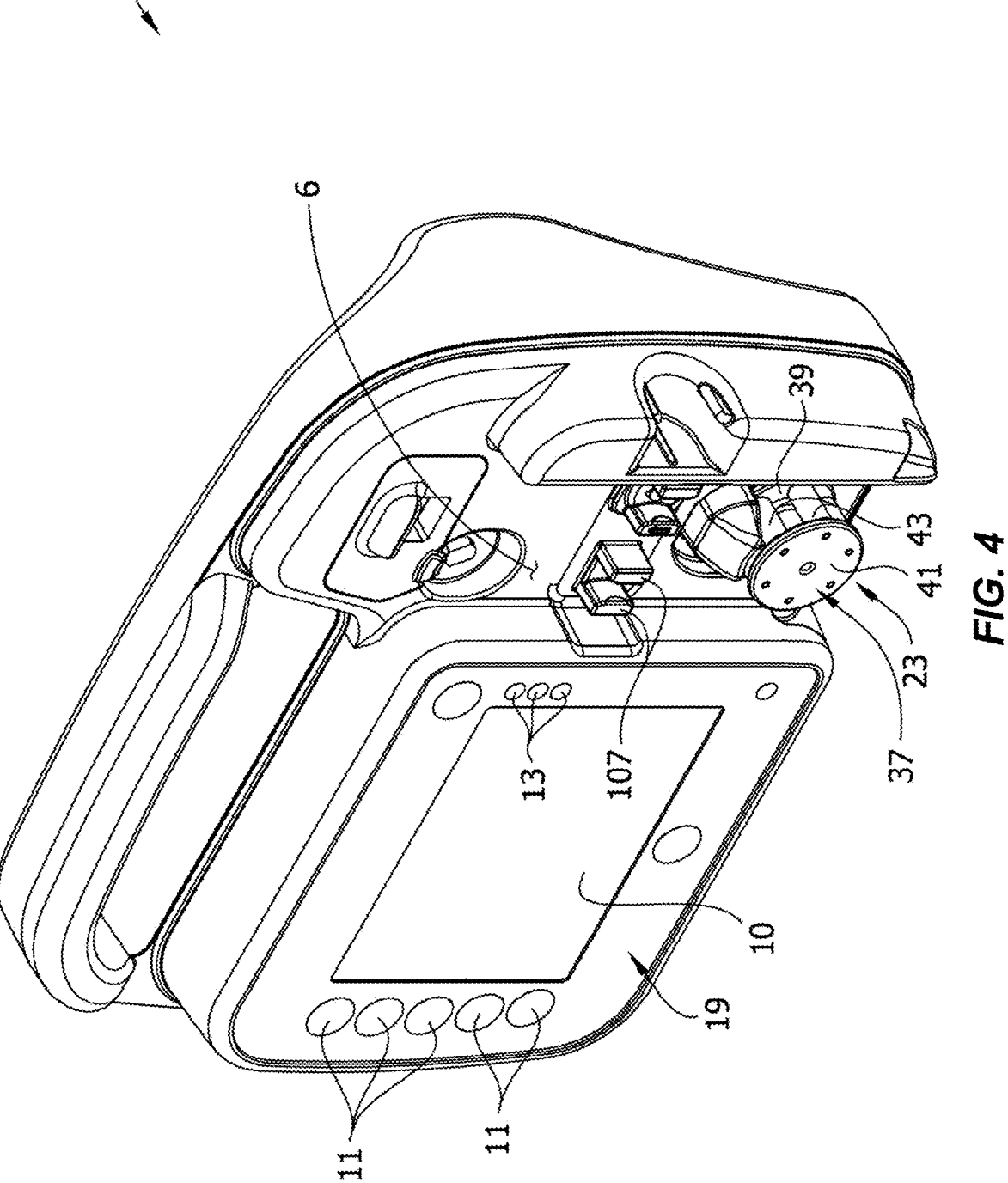
FIG. 4 is a front perspective view of the enteral feeding pump.

In some examples, the amount of feeding fluid that is delivered to the subject can be controlled by the number of rotations of the rotor 37 (in a counterclockwise direction as viewed in FIG. 3). In one aspect, the rotor 37 may include three rollers 43 so that each one-third of a rotation may deliver one aliquot of fluid to the subject. As each roller 43 first engages the tubing 45, it may pinch off the tubing thereby closing off an amount of fluid flowing forward (i.e., toward the subject) from the fluid coming from the feeding source. The roller 43 may continue in the counterclockwise rotation which may push the pinched-off volume of fluid forward of the roller, e.g., the aliquot, toward the subject. Finally, the leading roller 43 may release engagement with the tubing 45 at about the same time the trailing roller may engage the tubing for pinching it off for delivering the next aliquot of fluid, thus indirectly controlling the flow. When the microprocessor 89 receives a command to deliver a selected fluid flow rate, it may calculate the number of rotations within a given period of time that will deliver a number of aliquots producing the desired flow rate. The selected flow rate may be a rate that is input or selected by the doctor, nurse, or other caregiver, or may be a default feeding rate pre-programmed into the pump 1. However, aspects of the disclosure can provide an alternate, and improved, approach to controlling the fluid delivery from the syringe to the patient.

In examples of the present disclosure, the flow control apparatus may use approaches other than (in some cases, in addition to) aliquot counting (as described above) to adapt to estimates of the actual volume of fluid delivered at the beginning of a subinterval of the fluid feed, and may adjust the remaining flow of fluid during the subinterval to achieve the fluid volume objective. Such approaches may improve the accuracy of the volumes being fed and the time at which they are fed to improve stability of delivery throughout the feed and to more likely achieve on time completion of the feed.

In general, examples of aspects of the present disclosure may capture the initial time duration that the pump motor was turned on to deliver the first portion of fluid in a subinterval. Such examples may then estimate the volume that was actually delivered during that duration based upon the calculation of the movement of the linear potentiometer (as a proxy for the plunger 20) and may compare that to the volume that should be delivered over that duration of operation of the pump motor. The volume that should be delivered may be dependent upon the algorithmic time interval (interchangeably referred to as a "subinterval" in the examples below) for frequency of when the motor may turn on, and the user input rate. The algorithmic time interval for frequency of when the motor will turn on is typically for one (1) minute, but at lower rates and volumes this subinterval can increase as a minimum volume that the system can deliver may exceed the target for that subinterval and may delay until a minute time point, at which the volume to be delivered may be quantitatively below the value that has already been delivered. Inputting the user defined rate may be accomplished in either a continuous feeding system mode where an hourly rate is set, or a volume over time system mode where a volume and time may be independently set but from which an hourly rate can be calculated (e.g., volume input=30 mL, time input=15 minutes, therefore hourly rate=120 mL/hr.). With these two inputs, the objective volume to have been delivered in that subinterval can be determined (e.g., 120 mL/hr. means 2 mL may be delivered every minute). Based upon the estimated actual volume delivered, the flow control apparatus may adjust the volume to be delivered for the remainder of the subinterval (e.g., if 2.1 mL was delivered but the objective volume for the subinterval is 2 mL, then the remainder of the subinterval will target 1.9 mL delivery).

Additionally, example aspects of the disclosure can adjust the time at which the motor turns on to deliver this volume based on i) the amount of time the motor was turned on in the first portion of the subinterval and the estimate of the actual volume delivered (e.g., if 2.1 mL is actually fed and the target volume was 2 mL, then the system overdelivered by five (5) percent; therefore for the next time subinterval to meet the desired accumulated target volume (4 mL) the motor start time may be adjusted to turn on at 95 percent of the motor on time so that it can accurately feed the 1.9 mL at the second minute subinterval). At subsequent intervals, the actual accumulated volume may continually be compared to the anticipated accumulated target volumes, and the system may capture the predictive motor turn on times and average them over time to improve the stability of accurate volume and time delivery through the course of the feed.

Some benefits of this approach, aside from improving the accuracy of volume and time feed delivery, are that aspects of the disclosure can facilitate identification of each feed uniquely. This approach may facilitate the system to adjust the timing of the delivery to variables such as changes syringe brands, syringe sizes, syringe shelf life, degradation of feeding sets through the course of a feed, and changes in nutrition viscosity, density, and homogeneity.

Referring to FIG. 9, an example method 900 for fluid delivery is depicted. The method 900 can be implemented in a flow control apparatus 1. The flow control apparatus 1 includes tubing 77, a syringe 14 (also referred to herein as a "container") of fluid in fluid communication with the tubing 77, and a pump motor 27 operative to create a suction force on the fluid through the tubing 77 to deliver a dose of the fluid from the syringe 14 over a time interval. The dose includes aliquots (in the general sense, not limited to the amount of fluid pumped in one pass of a roller 43 over the tubing 77) of the fluid deliverable over subintervals of the time interval.

In method 900, at 910, the flow control apparatus may operate the pump motor for a first motor duration at a beginning of the subinterval to deliver less than an objective volume of the subinterval aliquot. The motor duration may be based on the objective volume of an aliquot to be delivered during a subinterval. In the example illustrated in FIG. 10 using a flow control apparatus 1 equipped with a peristaltic pump, the total interval is 8 min. (with 1 min. subintervals) and the total dose is 8 ml—corresponding to a rate of 60 ml/hr. (or 1 ml/min.), illustrated as dotted line 1002. The pump motor 27 may operate at an approximate rate of 3 ml/min (a characteristic of the flow control apparatus 1, and in some cases, a selectable characteristic).

Figure 10:
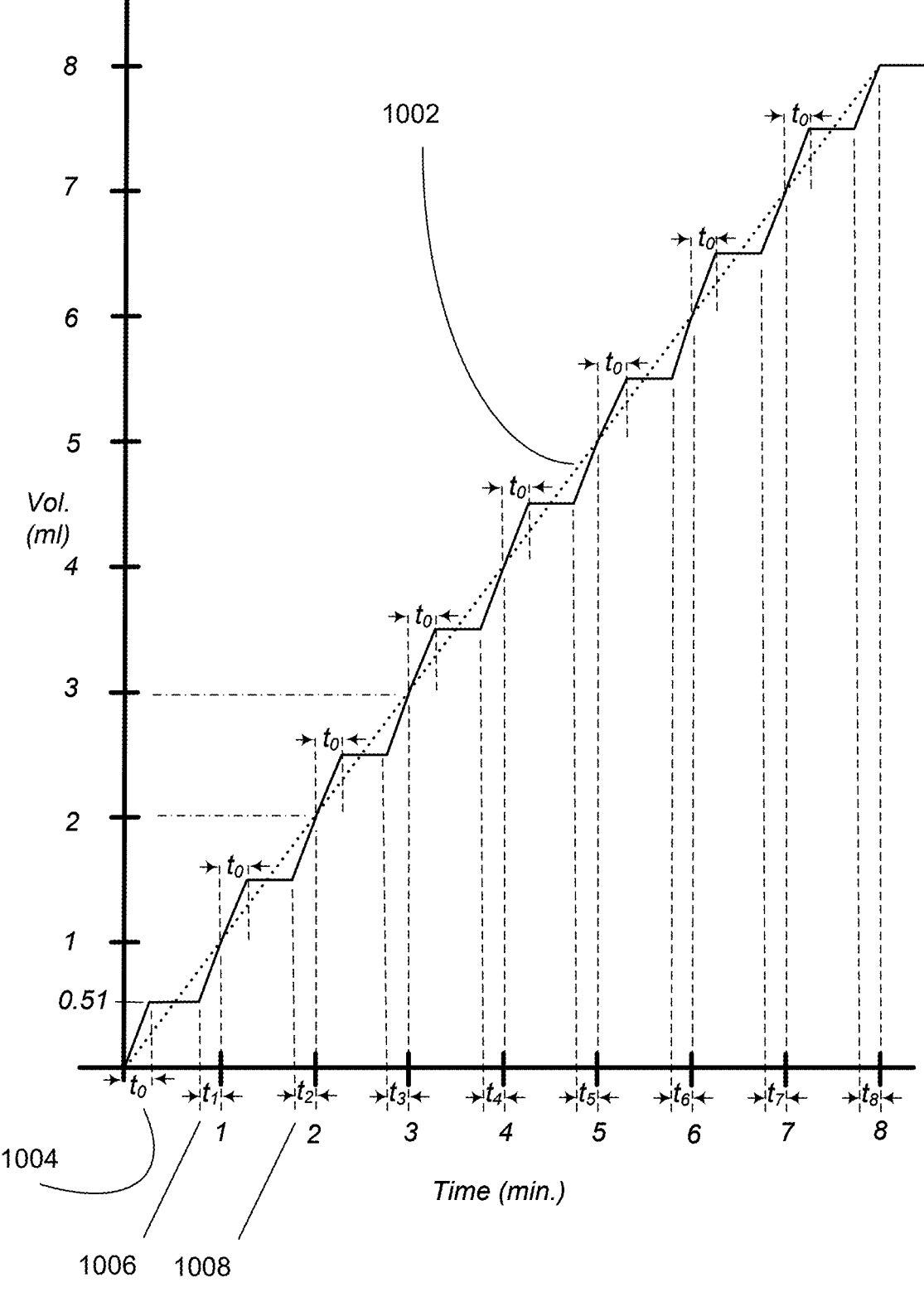
FIG. 10 illustrates a graph of operation of the example method of FIG. 9.

The first motor duration ("to" 1004 in FIG. 10) may be chosen as 10 sec. to deliver an objective volume of one half of the subinterval aliquot, i.e., 0.5 ml. In other examples, a different portion of the subinterval aliquot can be chosen, keeping in mind that the first motor duration serves to supply data in order to adjust a second motor duration to more accurately deliver the entire subinterval aliquot in the subinterval. In the example of FIG. 10, the same first motor duration is used for each subinterval, though this need not be the case.

In some examples, the objective volume may be a function of one or more of i) an objective delivery rate, and ii) an objective total amount of the fluid and an objective total time interval of the delivery. In some examples, such data can be input to the flow control apparatus 1 via a user interface, e.g., front panel 19 including display screen 10 (in some examples, a touch screen), buttons 11, and LEDs 13.

At 920, the flow control apparatus may sense a change in a position of a plunger (also referred to herein as a "first structure") of the syringe over the first motor duration. In the example of FIG. 10, contact 114 of the potentiometers 115 may be disposed on a movable portion of the holder 62, such as the slide plate 102, so that movement of the slide plate may cause the contact to move along the potentiometer 115. Because the barrel 18 may be held in a fixed position in the holder 62, as fluid is withdrawn from the barrel (also referred to herein as a "second structure"), the plunger 20 may move into the barrel. The flange 44 of the plunger 20 may be fixed to the slide plate 102 as the plunger moves into the barrel 18 causing the slide plate to move along the rails 98. Therefore, in an aspect, movement of the contact 114 may represent the movement of the plunger 20 relative to the barrel 18 and holder 62 caused by the feeding fluid being drawn out of the syringe 14. Stated another way, the movement of the contact 114 may correspond to the distance of advancement of the plunger 20 into the barrel 18.

At 930, the flow control apparatus may estimate a volume of fluid delivered over the first motor duration based on the sensed change in position. An outer diameter of the barrel 18 can be extrapolated from the angular position of the gate 106 to identify the appropriate calibration constant to use which relates change in plunger 20 position to fluid volume delivered. Alternatively, as the cross-sectional area of the internal cavity of the barrel 18 may be known from the detection of the syringe size, the potentiometer 115 can be calibrated so that the movement of the contact 114 indicates the volume of fluid expelled from the syringe 14. In particular, by knowing the inner diameter of the barrel 18 of the syringe 14, in combination with the distance the slide plate 102/plunger 20 has moved, the volume of fluid delivered from the syringe 14 can be determined. In the example of FIG. 10, the volume fed during the first motor duration "$t_0$" 1004 may be estimated to be 0.51 ml based on a sensed change in plunger 20 position, i.e., 0.01 ml over the objective volume of 0.50 ml.

In some cases, the an actual volume of fluid corresponding to a change in position of the slide plate 102/plunger 20 with respect to the barrel 18 is not simply the estimate $V=\pi r^2 \Delta h$—where V is estimated volume, r is nominal inner radius of the barrel, and $\Delta h$ is the relative change in position between the slide plate 102/plunger 20 with respect to barrel 18.

Factors such as variation in the inner cross-sectional area of the barrel (e.g., typically the interior radius decreases slightly from the open end of the barrel for manufacturing reasons), the nature of the fluid, and variations in the suction force on the fluid can affect the actual volume of fluid leaving the syringe. In particular, it has been observed that accuracy of the estimated volume can vary with flow rate and syringe size. Consider the data of TABLE 1 as an example of volume error data (between the estimated volume and the actual volume) collected across a population of trials for different flow rates and syringe sizes. Per TABLE 1, for a size 60 syringe at a 10 mL/hr. flow rate the estimated volume is an underestimation of the actual volume by 1.3%.

TABLE 1

| | Volume Error | | | | |
| Syringe | Approx Rate | | | | |
| Size | 1 mL/hr. | 10 mL/hr. | 50 mL/hr. | 100 mL/hr. | 200 mL/hr. |
|---|---|---|---|---|---|
| 6 | 2.0% | 1.8% | −4.7% | N/A | N/A |
| 12 | −3.3% | −1.1% | 1.2% | 4.5% | N/A |
| 35 | 2.8% | 0.9% | 0.9% | 0.5% | 0.6% |
| 60 | N/A | −1.3% | 0.7% | 0.4% | 0.4% |

Some examples of the technology disclosed herein adjust the volume estimation based on one or more of syringe type/size, flow rate, and the nature of the fluid being delivered. In some examples, adjusting can be by adding/subtracting a volume as appropriate. In some examples, adjusting can be by adding/subtracting from a nominal radius of the container. Each example for adjusting the estimated volume described herein can be combined with other examples, e.g., adjusting the radius by adding/subtracting based on position of the plunger in the syringe to account for manufacturing tapering of the radius, adjusting the volume by a scaling factor (described below) and by adding/subtracting an absolute correction.

In some examples of the technology disclosed herein, the estimated volume is determined by $V=\pi r^2 \times \Delta h$—where X is a correction coefficient dependent on one or more of syringe size, flow rate, and the nature of the fluid being delivered. In the example of TABLE 1, for the 60 mL syringe size, the following values of X shown in TABLE 2 can be used—with rate ranges chosen to overlap the flow rate data points of TABLE 1. For no error in the population, a factor of X=1.000 is used when adjusting an estimated volume in operation. For an underestimation, the percentage underestimation is added to X, e.g., a 1.1% underestimation (−1.1%) would result in X=1.011. For an overestimation, the percentage overestimation is subtracted from X, e.g., a 1.5% overestimation (1.5%) would result in X=0.095.

TABLE 2

| Rate | X |
|---|---|
| <5 mL/hr. | 1 |
| 5-25 mL/hr. | 1.013 |
| 25-75 mL/hr. | 0.993 |
| 75-125 mL/hr. | 0.996 |
| >125 mL/hr. | 0.996 |

For any container where the relative movement of a second structure of the container with respect to a first structure of the container determines a volume change in a substance held in the container, flow control apparatus may sense a change in a position of the first structure with respect to the second structure over the first motor duration, and may then estimate a volume of fluid delivered over the first motor duration based on the sensed change in position.

At 940, the flow control apparatus may determine a second motor duration to deliver a remainder of the objective volume of the aliquot, the second motor duration ending no later than the end of the subinterval and being determined based on the objective volume of the aliquot and the estimated volume of the aliquot. In the example of FIG. 10, where: $V_{a_n}$=volume delivered over motor duration during a subinterval throughout the feed; $V_{t_n}$=total objective volume to have been delivered at a given time point throughout the feed that is dependent upon the rate input by the user; $\mu_{t_n}$=average amount of time to motor was turned on for all subintervals up to a given time point throughout the feed; $t_n$=second motor duration prior to a subinterval time point; I=subinterval for the feed; and $s_n$=motor start time prior to the end of a subinterval for the second motor duration; the second motor duration may be:

$$\left(1 - \frac{V_{a_n} - V_{t_n}}{V_{t_n}}\right) * \mu_{t_n} = t_{n+1} \tag{1}$$

where, $$\mu_{t_n} = \frac{\sum t_n}{n+1}. \tag{2}$$

In the example of FIG. 10, the second motor duration (shown as "$t_1$" 1006 in FIG. 10) may be calculated using Equation (1) as:

$$\left(1 - \frac{0.51 \text{ mL} - 0.5 \text{ mL}}{0.5 \text{ mL}}\right) * 10 \text{ s} = 9.8 \text{ s} = t_1. \tag{3}$$

In the example of FIG. 10, the flow control apparatus initially overdelivered by 5 percent and took 10 seconds to deliver. In order to improve the accuracy of the volume fed to meet the desired volume at the first subinterval, 1 min., the flow control apparatus may correct the amount of time to start the motor to 9.8 sec. prior to the interval instead of 10 sec. so that volume delivered may be closer to the desired accumulated accuracy volume at one minute ($V_{t1}$=1 mL).

In the example of FIG. 10, the point in time "$s_n$" that the second motor duration should start in order to be complete by the end of the subinterval may be:

$$(I * (n + 1)) - t_{n+1} = s_n. \tag{4}$$

In the example of FIG. 10, this works out to be:

$$60 \text{ s} - 9.8 \text{ s} = 50.2 \text{ s} = s_1. \tag{5}$$

At 950, the flow control apparatus may operate the pump motor for the second motor duration targeting delivery of the remainder of the aliquot. In the example of FIG. 10, the flow control apparatus 1 operates the pump motor 27 for $t_1$=9.8 sec. prior to the end of the subinterval, i.e., starting at 50.2 sec.

In the example of FIG. 10, to calculate the motor duration to meet volume and time accuracy for the subsequent subinterval, 2 min., the estimated volume delivered at the 1 min. subinterval is captured as 1.05 mL ($V_{a_1}$=1.05 mL). Therefore, the following equations may be used to determine "$t_2$" 1008 and $s_2$:

$$\left(1 - \frac{V_{a_1} - V_{t_1}}{V_{t_1}}\right) * \mu_{t_1} = t_2 \tag{6}$$

-continued $$\left(1 - \frac{1.05 \text{ mL} - 1 \text{ mL}}{1 \text{ mL}}\right) * \left(\frac{10 + 9.8}{2}\right) = 9.405 \text{ s} = t_2 \tag{7}$$

$$(60 \text{ s} * 2) - 9.405 \text{ s} = 110.595 \text{ s} = s_2. \tag{8}$$

For subsequent subintervals in the example of FIG. 10, assume that the feed has progressed through the next-to-last subinterval with the following results: $V_{a_7}$=7.1 mL; $t_3$=8.25 s; $t_4$=8.75 s; $t_5$=9 s; $t_6$=9.25 s; $t_7$=8.875 s. For $t_8$ and $s_8$:

$$\left(1 - \frac{V_{a_7} - V_{t_7}}{V_{t_7}}\right) * \left(\frac{\sum t_7}{8}\right) = t_8 \tag{9}$$

$$(I * (7 + 1)) - t_8 = s_8 \tag{10}$$

$$\left(1 - \frac{7.1 \text{ mL} - 7 \text{ mL}}{7 \text{ mL}}\right) * \tag{11}$$

$$\left(\frac{10 + 9.5 + 9.8 + 8.25 + 8.75 + 9 + 9.25 + 8.875}{8}\right) = 9.178 \text{ s} = t_8$$

$$(60 * 8) - 9.178 = 470.822 \text{ s} = s_8. \tag{12}$$

In a second example, $V_{e_n}$=expected total target volume to have been delivered at a given time point; $V_{s_n}$=actual summation volume delivered up to the midpoint of a subinterval; $\sum m_n$=the summation of the motor on time for the duration of the feed with $m_n$ being equal to the motor duration at a given subinterval; $t_n$=second motor duration prior to interval time point; I=time subinterval for the feed; and $s_n$=motor start time. The second example may be characterized by the equations:

$$\left(V_{e_{n+1}} - V_{s_n}\right) \frac{\sum m_n}{V_{s_n}} = t_n \tag{13}$$

$$(I * (n + 1)) - t_n = s_n \tag{14}$$

Equation (13) and Equation (14) may calculate an average rate of delivery while the motor is turned on and then may calculate the time prior to the subinterval start time for the remaining volume difference to be delivered accurately on that subinterval time point and at the end of the feed. Equation (13) and Equation (14) may also be implemented in the fashion described in FIG. 9.

In the second example, an initial half aliquot fed at the first subinterval is 0.6 mL: $V_{s_0}$=0.6 mL. Motor on time to deliver the 0.6 mL was 10 seconds: $m_1$=10 s. As with the graph of FIG. 10, 1 min. subintervals are used; I=60 sec. or 1 min. A user inputted a rate of a volume and time that equates to a rate of 60 mL/hr. (e.g., 8 mL in 8 min.). $V_{e_1}$=1 mL, and all subintervals correspond to their volumes (e.g., interval at 10 minutes will have an expected volume of 10 mL), therefore:

$$V_{e_{n+1}} - V_{s_n} \frac{\sum m_n}{V_{s_n}} = \left(V_{e_1} - V_{s_0}\right) \frac{\sum m_0}{V_{s_0}} = \tag{15}$$

$$(1 \text{ mL} - 0.6 \text{ mL}) \frac{10 \text{ s}}{0.6 \text{ mL}} = 6.67 = t_1$$

-continued $$(I * (n+1)) - t_n = \qquad (16)$$

$$(60 * (0+1)) - t_1 = (60 \text{ s} * (0+1)) - 6.67 = 53.33 = s_1.$$

As for the last motor duration, assuming the cumulative motor duration to that point was 68 sec. and the volume delivered to that point was 7.4 mL, the last motor duration to provide accurate delivery would be:

$$V_{e_{n+1}} - V_{s_n}) \frac{\sum m_n}{V_{s_n}} = \left(V_{e_8} - V_{s_7}\right) \frac{\sum m_7}{V_{s_7}} = \qquad (17)$$

$$(8 \text{ mL} - 7.4 \text{ mL}) \frac{121 \text{ s}}{7.4 \text{ mL}} = 9.81 \text{ s} = t_7$$

$$(I * (n+1)) - t_n = (60 * (7+1)) - t_1 = (60 \text{ s} * (8)) - 9.81 = 470.19 = s_7. \qquad (18)$$

In some examples, the minimum volume that the system can accurately deliver at lower rates and volumes can be decreased. For example, an approach may be utilized in which finer use of motor controls builds the required pressure to move the syringe plunger slowly and precisely using partial motor rotor turns at defined time subintervals. As this mechanism applies to a flow control apparatus 1 as described herein, the minimized volume can facilitate a shorter motor delay time, resulting better individual feed cycle and overall accuracy.

For example, a user may input volume and time requirements and/or a rate equal to 6 ml/hr. To achieve this rate, the system needs to deliver a volume of 0.1 ml per minute. Using fine motor controls, the system may be able to build precise pressure and deliver target deliveries of this size during a typical 1 min. subinterval. Additionally, it can adjust time intervals to achieve slower (down to 1 ml/hr.) and faster rates as needed until the predictive algorithm becomes more appropriate.

Aspects of the disclosure may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects may be implemented with any number and organization of such components or modules. For example, various features or aspects are not limited to the specific computer-executable instructions or the specific components or modules illustrated in the figures and described herein. Other aspects may include different computer-executable instructions or components having more or less functionality than illustrated and described herein. Such aspects can be described as computer program products comprising memory storing instructions that when executed by a computer/processor are operative to perform the instructions.

Further, the order of execution or performance of the operations in any of the aspects illustrated and described herein is not essential, unless otherwise specified. That is, the operations may be performed in any order, unless otherwise specified, and aspects may include additional or fewer operations than those disclosed herein. For example, it is contemplated that executing or performing a particular operation before, contemporaneously with, or after another operation is within the scope of one or more aspects.

In operation, microprocessor 89 of the controller 72, shown in FIG. 8, may execute computer-executable instructions such as those illustrated in the figures to implement one or more aspects disclosed herein, such as data entry, display, motor control, and plunger sensing. Any of the various aspects may also be practiced in distributed computing environments where tasks are performed by remote processing devices that are linked through a communications network. In a distributed computing environment, program modules may be located in both local and remote computer storage media including memory storage devices.

Aspects of the present disclosure may be implemented using hardware, software, or a combination thereof and may be implemented in one or more computer systems or other processing systems. In one aspect, the disclosure is directed toward one or more computer systems capable of carrying out the functionality described herein. An example of such a computer system 1100 is shown in FIG. 11.

Figure 11:
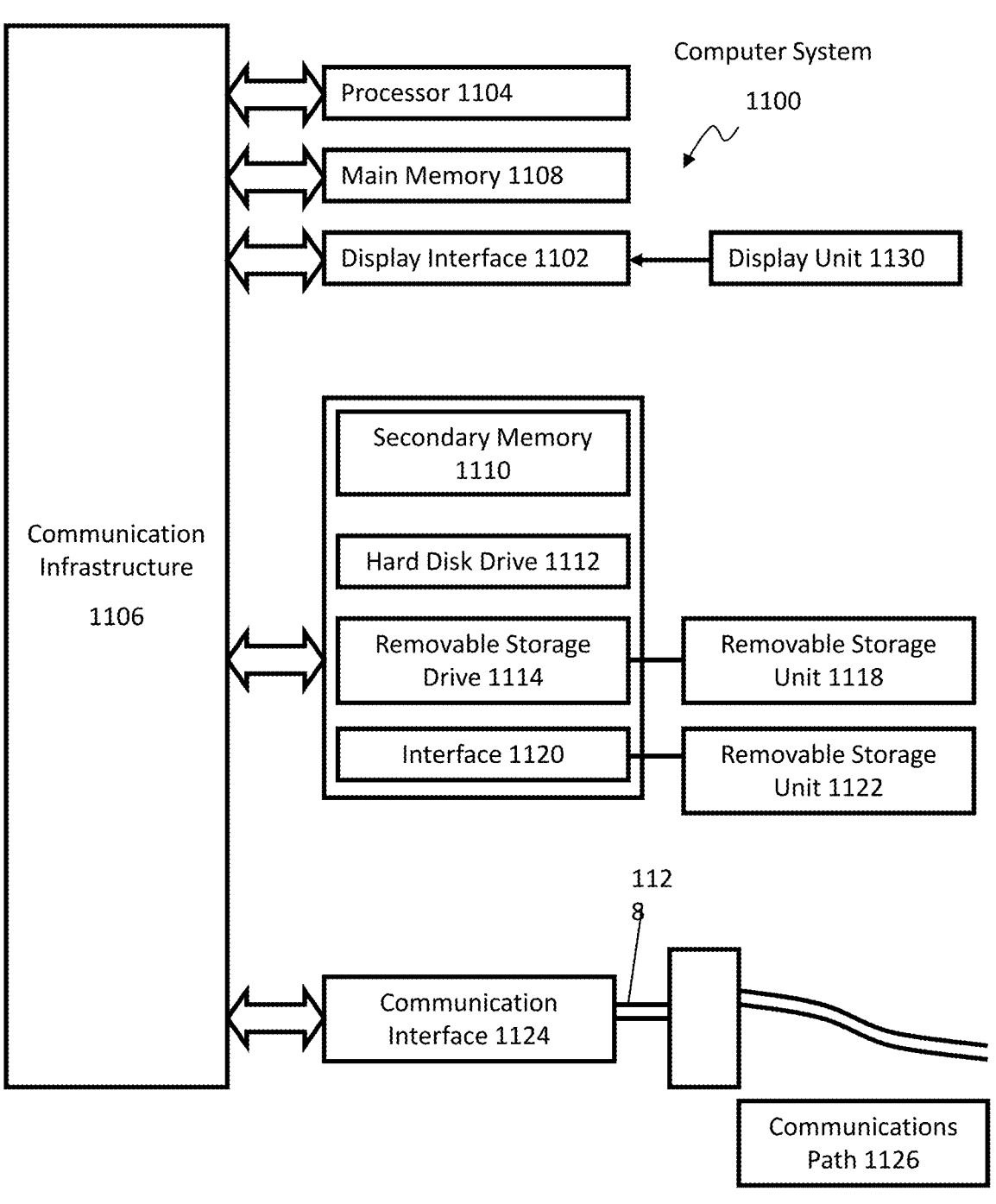
FIG. 11 presents an example system diagram of various hardware components and other features, for use in accordance with aspects of the present disclosure.

FIG. 11 presents an example system diagram of various hardware components and other features, for use in accordance with an aspect of the present disclosure. Aspects of the present disclosure may be implemented using hardware, software, or a combination thereof and may be implemented in one or more computer systems or other processing systems. In one exemplary variation, aspects of the disclosure are directed toward one or more computer systems capable of carrying out the functionality described herein. An example of such a computer system 1100 is shown in FIG. 11.

Computer system 1100 includes one or more processors, such as processor 1104. The processor 1104 is connected to a communication infrastructure 1106 (e.g., a communications bus, cross-over bar, or network). Various software aspects are described in terms of this example computer system. After reading this description, it will become apparent to a person skilled in the relevant art(s) how to implement aspects of the disclosure using other computer systems and/or architectures.

Computer system 1100 may include a display interface 1102 that forwards graphics, text, and other data from the communication infrastructure 1106 (or from a frame buffer not shown) for display on a display unit 1130. Computer system 1100 also includes a main memory 1108, preferably random-access memory (RAM), and may also include a secondary memory 1110. The secondary memory 1110 may include, for example, a hard disk drive 1112 and/or a removable storage drive 1114, representing a floppy disk drive, a magnetic tape drive, an optical disk drive, etc. The removable storage drive 1114 reads from and/or writes to a removable storage unit 1118 in a well-known manner. Removable storage unit 1118, represents a floppy disk, magnetic tape, optical disk, etc., which is read by and written to removable storage drive 1114. As will be appreciated, the removable storage unit 1118 includes a computer usable storage medium having stored therein computer software and/or data.

In alternative aspects, secondary memory 1110 may include other similar devices for allowing computer programs or other instructions to be loaded into computer system 1100. Such devices may include, for example, a removable storage unit 1122 and an interface 1120. Examples of such may include a program cartridge and cartridge interface (such as that found in video game devices), a removable memory chip (such as an erasable programmable read only memory (EPROM), or programmable read only memory (PROM)) and associated socket, and other removable storage units 1122 and interfaces 1120, which allow software and data to be transferred from the removable storage unit 1122 to computer system 1100.

Computer system 1100 may also include a communications interface 1124. Communications interface 1124 allows software and data to be transferred between computer system 1100 and external devices. Examples of communications interface 1124 may include a modem, a network interface (such as an Ethernet card), a communications port, a Personal Computer Memory Card International Association (PCMCIA) slot and card, etc. Software and data transferred via communications interface 1124 are in the form of signals 1128, which may be electronic, electromagnetic, optical, or other signals capable of being received by communications interface 1124. These signals 1128 are provided to communications interface 1124 via a communications path (e.g., channel) 1126. This path 1126 carries signals 1128 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1180, a hard disk installed in hard disk drive 1170, and signals 1128. These computer program products provide software to the computer system 1100. Aspects of the disclosure are directed to such computer program products.

Computer programs (also referred to as computer control logic) are stored in main memory 1108 and/or secondary memory 1110. Computer programs may also be received via communications interface 1124. Such computer programs, when executed, enable the computer system 1100 to perform various features in accordance with aspects of the present disclosure, as discussed herein. In particular, the computer programs, when executed, enable the processor 1104 to perform such features. Accordingly, such computer programs represent controllers of the computer system 1100.

In variations where aspects of the disclosure are implemented using software, the software may be stored in a computer program product and loaded into computer system 1100 using removable storage drive 1114, hard drive 1112, or communications interface 1120. The control logic (software), when executed by the processor 1104, causes the processor 1104 to perform the functions in accordance with aspects of the disclosure as described herein. In another variation, aspects are implemented primarily in hardware using, for example, hardware components, such as application specific integrated circuits (ASICs). Implementation of the hardware state machine so as to perform the functions described herein will be apparent to persons skilled in the relevant art(s).

In yet another example variation, aspects of the disclosure are implemented using a combination of both hardware and software.

Figure 12:
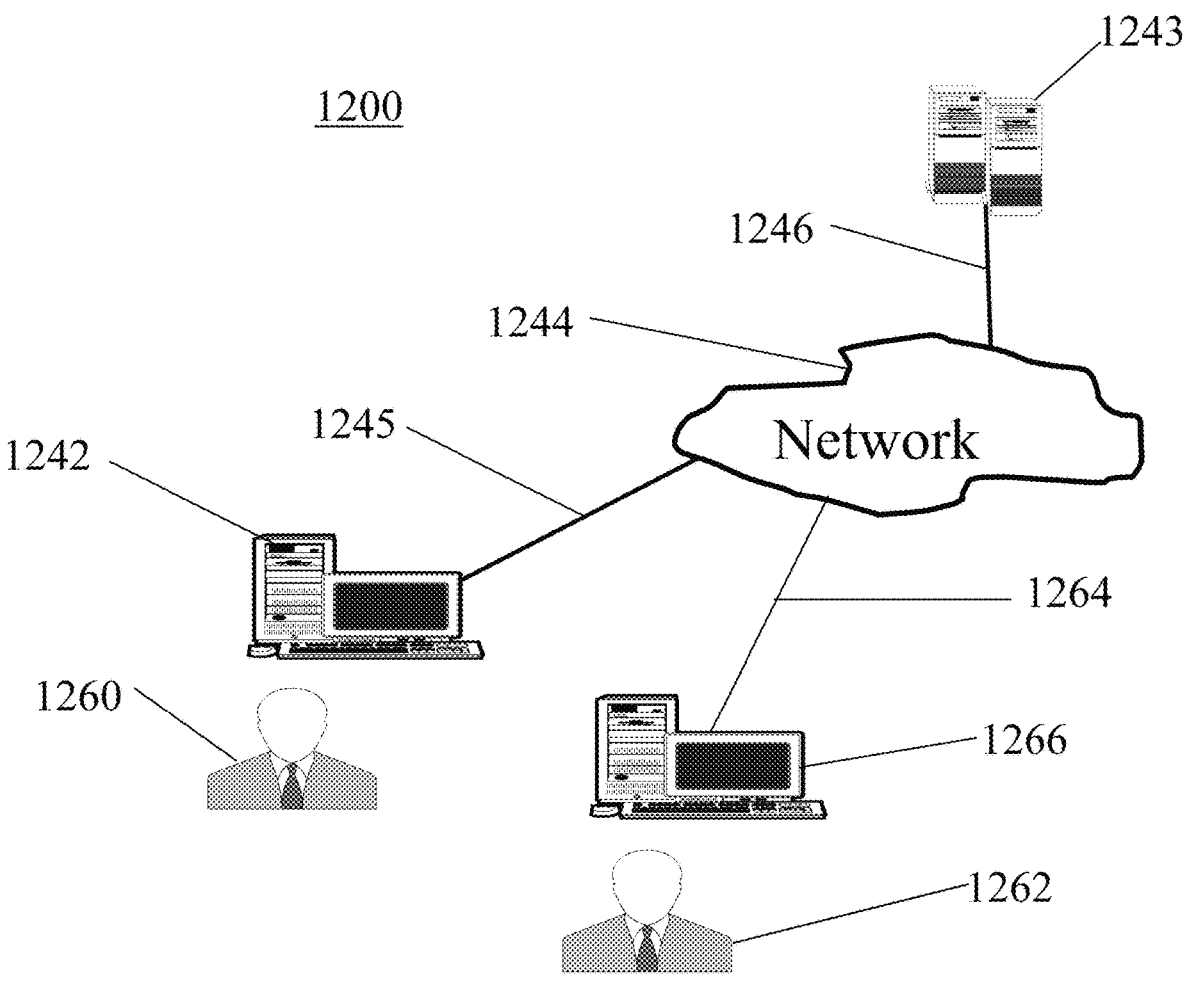
FIG. 12 is a block diagram of various example system components, in accordance with aspects of the present disclosure.

FIG. 12 is a block diagram of various example system components, in accordance with an aspect of the present disclosure. FIG. 12 shows a communication system 1200 usable in accordance with the present disclosure. The communication system 1200 includes one or more accessors 1260, 1262 (also referred to interchangeably herein as one or more "users") and one or more terminals 1242, 1266. In one aspect, data for use in accordance with aspects of the present disclosure is, for example, input and/or accessed by accessors 1260, 1262 via terminals 1242, 1266, such as personal computers (PCs), minicomputers, mainframe computers, microcomputers, telephonic devices, or wireless devices, such as personal digital assistants ("PDAs") or a hand-held wireless devices coupled to a server 1243, such as a PC, minicomputer, mainframe computer, microcomputer, or other device having a processor and a repository for data and/or connection to a repository for data, via, for example, a network 1244, such as the Internet or an intranet, and couplings 1245, 1246, 1264. The couplings 1245, 1246, 1264 include, for example, wired, wireless, or fiberoptic links. In another example variation, the method and system in accordance with aspects of the present disclosure operate in a stand-alone environment, such as on a single terminal.

The aspects of the disclosure discussed herein can also be described and implemented in the context of computer-readable storage medium storing computer-executable instructions. Computer-readable storage media includes computer storage media and communication media. For example, flash memory drives, digital versatile discs (DVDs), compact discs (CDs), floppy disks, and tape cassettes. Computer-readable storage media can include volatile and nonvolatile, removable and non-removable media implemented in any method or technology for storage of information such as computer readable instructions, data structures, modules, or other data.

It will be appreciated that various implementations of the above-disclosed and other features and functions, or alternatives or varieties thereof, can be desirably combined into many other different systems or applications. Also, that various presently unforeseen or unanticipated alternatives, modifications, variations, or improvements therein can be subsequently made by those skilled in the art which are also intended to be encompassed by the following claims.

When introducing elements of the present disclosure or the aspects(s) thereof, the articles "a", "an", "the" and "said" are intended to mean that there are one or more of the elements. The terms "comprising", "including" and "having" are intended to be inclusive and mean that there may be additional elements other than the listed elements.

Throughout the present disclosure, the terms "substantially" or "approximately" may be used as a modifier for a geometric relationship between elements or for the shape of an element or component. While the terms substantially or approximately are not limited to a specific variation and may cover any variation that is understood by one of ordinary skill in the art to be an acceptable variation, some examples are provided as follows. In one example, the term substantially or approximately may include a variation of less than 10% of the dimension of the object or component. In another example, the term substantially or approximately may include a variation of less than 5% of the object or component. If the term substantially or approximately is used to define the angular relationship of one element to another element, one non-limiting example of the term substantially or approximately may include a variation of 5 degrees or less. These examples are not intended to be limiting and may be increased or decreased based on the understanding of acceptable limits to one of skill in the relevant art.

For purposes of the present disclosure, directional terms are expressed generally with relation to a standard frame of reference when the system and apparatus described herein is installed in an in-use orientation. Further, in order to provide context to the current disclosure, a broad overview of the discovered deficiencies of various systems and an example implementation of the current disclosure and the advantages provided by the disclosure are described below. Further details of example implementations of the current disclosure are described in detail with reference to the figures below.

The terms "first," "second," "third," and "fourth," among other numeric values, may be used in the present disclosure. It will be understood that, unless otherwise noted, those terms are used in their relative sense only. In particular, in some aspects, certain components may be present in interchangeable and/or identical multiples (e.g., pairs). For these components, the designation of first, second, third, and/or fourth may be applied to the components merely as a matter of convenience in the description of one or more of the aspects of the disclosure.

As various changes could be made in the above constructions without departing from the scope of the disclosure, it is intended that all matter contained in the above description and shown in the accompanying drawings shall be interpreted as illustrative and not in a limiting sense.

What is claimed is:

1. A method of fluid delivery implemented in a flow control apparatus comprising tubing, a container of fluid in fluid communication with the tubing, and a pump motor operative to create a suction force on the fluid through the tubing to deliver a dose of the fluid from the container over a time interval, the dose comprising aliquots of the fluid deliverable over subintervals of the time interval, the method comprising:

operating, based on an objective volume of an aliquot to be delivered during a subinterval, the pump motor for a first motor duration at a beginning of the subinterval to deliver less than the objective volume of the aliquot;

sensing a change in a position of a first structure of the container relative to the position of a second structure of the container over the first motor duration;

estimating a volume of fluid delivered over the first motor duration based on the sensed change in position;

determining a second motor duration to deliver a remainder of the objective volume of the aliquot, the second motor duration ending no later than the end of the subinterval and being determined based on the objective volume of the aliquot and the estimated volume of the aliquot; and operating the pump motor for the second motor duration targeting delivery of the remainder of the aliquot.

2. The method of claim 1, wherein the container is a syringe, the first structure is a syringe plunger, and the second structure is a syringe barrel.

3. The method of claim 1, wherein a pump of the pump motor is a peristaltic pump.

4. The method of claim 1, wherein estimating the volume comprises adjusting the estimated volume based on one or more of a size of the container, a flow rate of the fluid while the pump motor is operating, and the fluid.

5. The method of claim 4, wherein the adjusting is based on actual delivered volume across a population of containers of similar one or more or size of the container, flow rate of the fluid while the pump motor is operating, and the fluid.

6. The method of claim 1, wherein the objective volume is a function of one or more of i) an objective delivery rate, and ii) an objective total amount of the fluid and an objective total time interval of the delivery.

7. The method of claim 1, wherein the objective volume is based on data entry via a user interface of the flow control apparatus.

8. The method of claim 1, wherein the second motor duration is based on a rate of volume of fluid delivered over time as determined from a cumulative estimated actual volume of fluid delivered for the dose and the cumulative motor duration for the dose.

9. The method of claim 1, wherein sensing a change of position of the first structure of the container relative to the position of a second structure of the container is performed using a linear potentiometer.

10. The method of claim 1, further comprising, for subsequent aliquots:

operating, based on a second objective volume of an aliquot to be delivered during a subsequent subinterval, the pump motor for a third motor duration at the beginning of the subsequent subinterval to deliver less than the second objective volume of the aliquot;

sensing a second change in a position of a first structure of the container relative to the position of a second structure of the container;

estimating a volume of fluid delivered over the third motor duration based on the sensed second change in position;

determining a fourth motor duration to deliver a remainder of the second objective volume of the aliquot, the fourth motor duration ending no later than the end of the subsequent subinterval and determined based on a difference between a cumulative objective volume of the aliquot at the end of the third motor duration and a cumulative estimated volume of the aliquot at the end of the third motor duration; and operating the pump motor for the fourth motor duration targeting delivery of the remainder of the subsequent aliquot.

11. A flow control apparatus for fluid delivery comprising:

a processor;

memory in communication with the processor and storing instructions;

tubing;

a container in fluid communication with the tubing and adapted to store a fluid; and a pump motor operative, under control of the instructions executed by the processor, to create a suction force on a fluid in the container through the tubing to deliver a dose of the fluid from the container over a time interval, the dose comprising aliquots of the fluid deliverable over subintervals of the time interval, wherein the instructions, when executed by the processor are operative to cause the flow control apparatus to:

operate, based on an objective volume of an aliquot to be delivered during a subinterval, the pump motor for a first motor duration at a beginning of the subinterval to deliver less than the objective volume of the aliquot;

sense a change in a position of a first structure of the container relative to the position of a second structure of the container over the first motor duration;

estimate a volume of fluid delivered over the first motor duration based on the sensed change in position;

determine a second motor duration to deliver a remainder of the objective volume of the aliquot, the second motor duration ending no later than the end of the subinterval and being determined based on a difference between the objective volume of the aliquot and the estimated volume of the aliquot; and operate the pump motor for the second motor duration targeting delivery of the remainder of the aliquot.

12. The apparatus of claim 11, wherein the container is a syringe, the first structure is a syringe plunger, and the second structure is a syringe barrel.

13. The apparatus of claim 11, wherein a pump of the pump motor is a peristaltic pump.

14. The apparatus of claim 11, wherein the objective volume is a function of one or more of i) an objective delivery rate, and ii) an objective total amount of the fluid and an objective total time interval of the delivery.

15. The apparatus of claim 11, wherein the objective volume is based on data entry via a user interface of the apparatus.

16. The apparatus of claim 11, wherein the second motor duration is based on a rate of volume of fluid delivered over time as determined from a cumulative estimated actual volume of fluid delivered for the dose and the cumulative motor duration for the dose.

17. The apparatus of claim 11, further comprising:

a linear potentiometer, wherein sensing a change of position of the first structure of the container relative to the position of a second structure of the container is performed using the linear potentiometer.

18. The apparatus of claim 11, further comprising, wherein the instructions, when executed by the processor are further operative to cause the flow control apparatus to, for subsequent aliquots:

operate, based on a second objective volume of an aliquot to be delivered during a subsequent subinterval, the pump motor for a third motor duration at the beginning of the subsequent subinterval to deliver less than the second objective volume of the aliquot;

sense a second change in a position of a first structure of the container relative to the position of a second structure of the container over the third motor duration;

estimate a volume of fluid delivered over the third motor duration based on the sensed second change in position;

determine a fourth motor duration to deliver a remainder of the second objective volume of the aliquot, the fourth motor duration ending no later than the end of the subsequent subinterval and determined based on a difference between a cumulative objective volume of the aliquot at the end of the third motor duration and a cumulative estimated volume of the aliquot at the end of the third motor duration; and operate the pump motor for the fourth motor duration targeting delivery of the remainder of the subsequent aliquot.

19. A computer program product for controlling fluid delivery in a flow control apparatus, the flow control apparatus comprising a processor; memory in communication with the processor and storing instructions; tubing; a container in fluid communication with the tubing and adapted to store a fluid; and a pump motor operative, under control of the instructions executed by the processor, to create a suction force on a fluid in the container through the tubing to deliver a dose of the fluid from the container over a time interval, the dose comprising aliquots of the fluid deliverable over subintervals of the time interval, the computer program product comprising instructions that when executed by a processer are operative to cause the flow control apparatus to:

operate, based on an objective volume of an aliquot to be delivered during a subinterval, the pump motor for a first motor duration at a beginning of the subinterval to deliver less than the objective volume of the aliquot;

sense a change in a position of a first structure of the container relative to the position of a second structure of the container over the first motor duration;

estimate a volume of fluid delivered over the first motor duration based on the sensed change in position;

determine a second motor duration to deliver a remainder of the objective volume of the aliquot, the second motor duration ending no later than the end of the subinterval and being determined based on a difference between the objective volume of the aliquot and the estimated volume of the aliquot; and operate the pump motor for the second motor duration targeting delivery of the remainder of the aliquot.

20. The computer program product of claim 19, wherein the container is a syringe, the first structure is a syringe plunger, and the second structure is a syringe barrel.

21. The computer program product of claim 19, wherein a pump of the pump motor is a peristaltic pump.

22. The computer program product of claim 19, wherein the objective volume is a function of one or more of i) an objective delivery rate, and ii) an objective total amount of the fluid and an objective total time interval of the delivery.

23. The computer program product of claim 19, wherein the objective volume is based on data entry via a user interface of the flow control apparatus.

24. The computer program product of claim 19, wherein the second motor duration is based on a rate of volume of fluid delivered over time as determined from a cumulative estimated actual volume of fluid delivered for the dose and the cumulative motor duration for the dose.

25. The computer program product of claim 19, further comprising, wherein the instructions, when executed by the processer are further operative to cause the flow control apparatus to, for subsequent aliquots:

operate, based on a second objective volume of an aliquot to be delivered during a subsequent subinterval, the pump motor for a third motor duration at the beginning of the subsequent subinterval to deliver less than the second objective volume of the aliquot;

sense a second change in a position of a position of a first structure of the container relative to the position of a second structure of the container over the third motor duration;

estimate a volume of fluid delivered over the third motor duration based on the sensed second change in position;

determine a fourth motor duration to deliver a remainder of the second objective volume of the aliquot, the fourth motor duration ending no later than the end of the subsequent subinterval and determined based on a difference between a cumulative objective volume of the aliquot at the end of the third motor duration and a cumulative estimated volume of the aliquot at the end of the third motor duration; and operate the pump motor for the fourth motor duration targeting delivery of the remainder of the subsequent aliquot.

* * * * *